United States Patent [19]
Ciardelli et al.

[11] Patent Number: 5,837,816
[45] Date of Patent: Nov. 17, 1998

[54] INTERLEUKIN-2 RECEPTOR SUBUNIT ECTODOMAIN FUSION PROTEIN COMPRISING A LEUCINE ZIPPER DOMAIN

[75] Inventors: Thomas L. Ciardelli, Sharon, Vt.; Kirk Johnson, Moraga, Calif.

[73] Assignees: Chiron Corporation, Emeryville, Calif.; Trustee of Dartmouth College, Hanover, N.H.

[21] Appl. No.: 474,741

[22] Filed: Jun. 7, 1995

Related U.S. Application Data

[63] Continuation-in-part of Ser. No. 438,259, May 10, 1995, abandoned.

[51] Int. Cl.$^6$ .................. C07K 14/435; C07K 14/705; C07K 14/715; C12N 15/12
[52] U.S. Cl. .................. 530/350; 435/69.1; 435/320.1; 536/23.4; 536/24.1; 514/2
[58] Field of Search .................. 530/350; 435/69.1, 435/320.1, 240.2, 325, 7.1; 536/23.4; 514/2

[56] References Cited

U.S. PATENT DOCUMENTS 5,510,259 4/1996 Sugamura et al. .................. 435/240

FOREIGN PATENT DOCUMENTS

94/10308 5/1994 WIPO .
WO 94/29332 12/1994 WIPO .

OTHER PUBLICATIONS

Hodges, R.S. (1992) Current Biology 2:122–124.
Barclay et al. (1993) The Leucocyte Antigen Facts Book, Academic Press Inc., San Diego, CA pp. 22–23.
Bowie et al. (1990) Science 247:1307–1310.
Chang, et al., *Proc. Natl. Acad. Sci.* (1994) 91:11408–11412.
Wu, et al., *J. Immun. Methods* (1995) 183:127–130.
Wu, et al., *J. Bio. Chem.*, (1995) 270:16039–16044.
Wu, et al., *Protein Engineering* (1994) 7:1137–1144.
Blondel et al., *Protein Enginerring* (1991) 4:457.
Buckland et al., *J. Gen. Virol.* (1992) 73:1703.
Cohen et al., (1994) *Science* 263:488–498.
Graddis et al., (1993) *Biochemistry* 32:12664–12670.
Harbury et al., (1993) *Science* 262:1401–1408.
Hu et al., *Science* (1900) 250:1400.
Johnson et al., (1993) *Eur. Cytokine Netw.* 5:23–34.
Kostelny et al., (1992) *J. Immunol.* 148:1547–1553.
Lovejoy et al. (1993) *Science* 259:1288–1293.
O'Niel et al., (1990) *Science* 250:646–651.
O'Shea et al., *Science* (1989) 245:646.
Pack et al., (1992) *Biochemistry* 31:1579–1584.
Rabindran et al., *Science* (1993) 259:230.
Turner et al., *Science* (1989) 243:1689.
Wu et al., *Peptides: Chemistry, Structure & Biology* (Proceedings of the 13th American peptide Symposium) R.S. Hodges and J.A. Smith, Eds. (ESCOM, Leiden, 1994) pp. 1038–1040.
Zhu et al., (1993) *Prot. Sci.* 2:383–394.
Zhu et al., (1992) *Int. J. Prot. Pep. Res.* 40:171–192.

*Primary Examiner*—Stephen Walsh
*Assistant Examiner*—Michael Pak
*Attorney, Agent, or Firm*—Donald Pochopien; Jane E. R. Potter; Robert P. Blackburn

[57] ABSTRACT

Coiled-coil molecular recognition is a primary mode of subunit assembly in a large variety of naturally occurring macromolecular complexes. Here we report the use of coiled-coil mediated solution assembly to form a stable, heteromeric complex of Interleukin-2 receptor ectodomains that binds IL-2 cooperatively and with an affinity approaching the comparable cell surface complex. Cross-linking of homomeric or heteromeric receptor subunits is the common signal transmission mechanism employed by hematopoietin receptors. Individual receptor ectodomains, however, often do not bind ligand with measurable affinity. The claimed invention is useful for coiled-coil mediated assembly of receptor complexes for solution analysis. It also shows that hetero-oligomeric complexes can be formed using a leucine zipper domain.

11 Claims, 4 Drawing Sheets

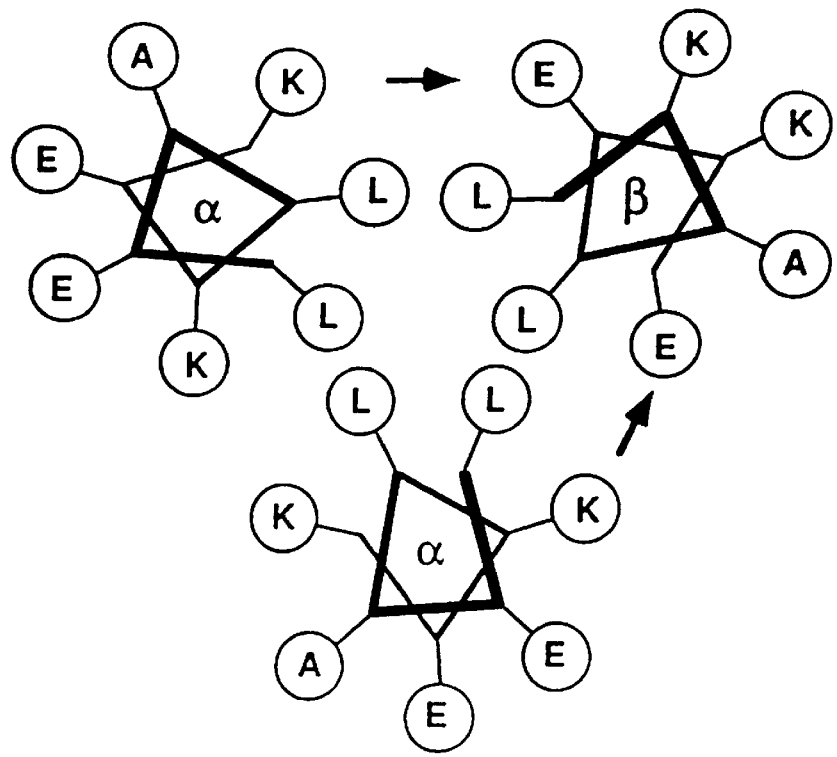
FIG. IA
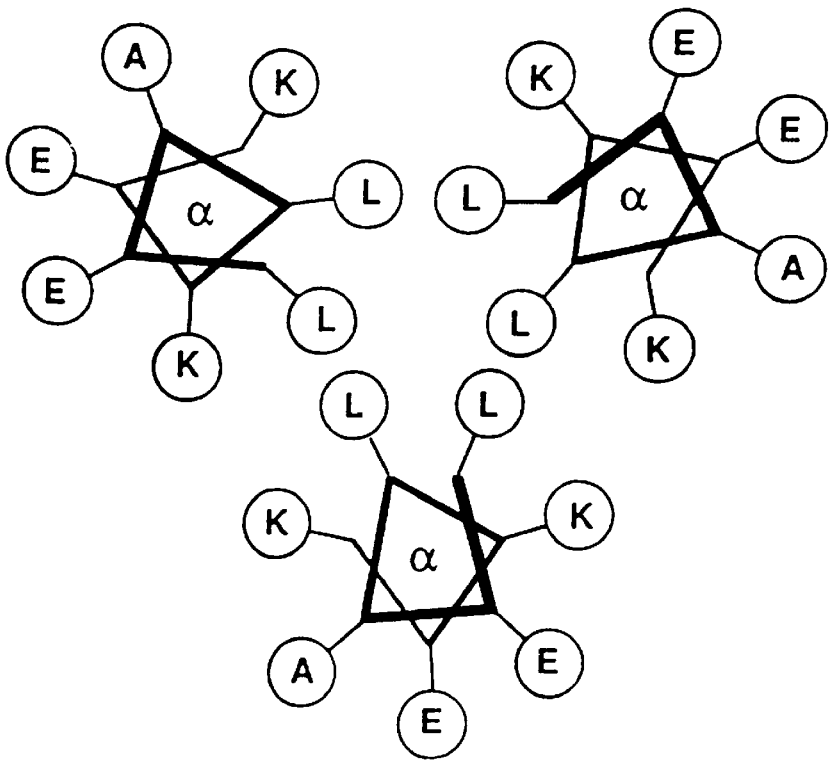
FIG. IB

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:1:

Leu  Glu  Ala  Leu  Lys  Glu  Lys
    1                        5

( 2 ) INFORMATION FOR SEQ ID NO:2:

( i ) SEQUENCE CHARACTERISTICS:
        ( A ) LENGTH: 7 amino acids
        ( B ) TYPE: amino acid
        ( C ) STRANDEDNESS: single ( D ) TOPOLOGY: linear ( i i ) MOLECULE TYPE: protein ( x i ) SEQUENCE DESCRIPTION: SEQ ID NO:2:

Leu  Lys  Ala  Lys  Glu  Lys  Glu
    1                     5

( 2 ) INFORMATION FOR SEQ ID NO:3:

( i ) SEQUENCE CHARACTERISTICS:
            ( A ) LENGTH: 7 amino acids
            ( B ) TYPE: amino acid
            ( C ) STRANDEDNESS: single
            ( D ) TOPOLOGY: linear ( i i ) MOLECULE TYPE: protein ( x i ) SEQUENCE DESCRIPTION: SEQ ID NO:3:

Leu  Glu  Ala  Leu  Glu  Lys  Lys
    1                     5

( 2 ) INFORMATION FOR SEQ ID NO:4:

( i ) SEQUENCE CHARACTERISTICS:
            ( A ) LENGTH: 7 amino acids
            ( B ) TYPE: amino acid
            ( C ) STRANDEDNESS: single
            ( D ) TOPOLOGY: linear ( i i ) MOLECULE TYPE: protein ( x i ) SEQUENCE DESCRIPTION: SEQ ID NO:4:

Leu  Lys  Ala  Leu  Glu  Lys  Glu
    1                     5

( 2 ) INFORMATION FOR SEQ ID NO:5:

( i ) SEQUENCE CHARACTERISTICS:
            ( A ) LENGTH: 6 amino acids
            ( B ) TYPE: amino acid
            ( C ) STRANDEDNESS: single
            ( D ) TOPOLOGY: linear ( i i ) MOLECULE TYPE: protein ( x i ) SEQUENCE DESCRIPTION: SEQ ID NO:5:

Glu  Tyr  Met  Pro  Met  Glu
    1                     5

INTERLEUKIN-2 RECEPTOR SUBUNIT ECTODOMAIN FUSION PROTEIN COMPRISING A LEUCINE ZIPPER DOMAIN

CROSS-REFERENCE TO RELATED APPLICATION

The present application is a continuation-in-part of U.S. Ser. No. 08/438,259, filed May 10, 1995, now abandoned. Work described herein was supported, in part, funding from the NIH in grant number R01AI34331.

TECHNICAL FIELD OF THE INVENTION

The present invention relates to a method of preparing soluble oligomeric proteins using recombinant DNA technology.

BACKGROUND OF THE INVENTION

The biological activity of proteins is dependent upon proper tertiary and quaternary structure, or conformation. Many proteins exist as oligomers (structure comprised of two or more polypeptide chains) in their native form. Such oligomers are often stabilized by non-covalent interactions, and are thus dependent on proper tertiary structure of the individual peptides. Expression of a recombinant protein in biologically active form, exhibiting the proper tertiary and quaternary structure, by host cells which do not normally express a native form of the protein, frequently presents a significant challenge. Of particular interest in recombinant protein technology is expression of proteins that are membrane-bound in the biologically active form, as soluble proteins. Soluble proteins are useful as therapeutic agents, and in other applications requiring large quantities of highly purified proteins.

Soluble forms of transmembrane proteins have been prepared by deleting the transmembrane and intracytoplasmic domains, and adding an appropriate signal peptide to enable secretion of the soluble form of the protein (Smith et al., Science 238:1704, 1987; Treiger et al., J. Immunol. 136:4099, 1986). Some soluble proteins have been expressed as fusion proteins in which the extracellular domain of the membrane protein is joined to an immunoglobulin heavy chain constant region (Fanslow et al., J. Immunol. 149:65, 1992; Noelle et al., Proc. Natl. Acad. Sci. U.S.A. 89:6550, 1992), or with the extracellular domain of the murine T lymphocyte antigen CD8 (Hollenbaugh et al., EMBO J. 11:4313, 1992). However, such soluble proteins may not be biologically active due to improper tertiary and/or quaternary structure. Some soluble forms of transmembrane proteins may be biologically active, but poorly expressed, or unstable under the conditions of expression or purification, due to changes in structure as a result of deletion of a portion or portions of the protein.

Leucine zipper is a term that is used to refer to a repetitive heptad motif containing four to five leucine residues present as a conserved domain in several proteins. Leucine zippers fold as short, parallel coiled coils, and are believed to be responsible for oligomerization of the proteins of which they form a domain. Sequences derived from the fos and jun leucine zippers have been used in the formation of bispecific antibodies by expression of DNA encoding the $V_L$ and $V_H$ regions of antibodies as fusion proteins with the leucine zipper sequences. (Kostelny et al., J. Immunol. 148:1547, 1992) leucine zipper sequences have also been used to replace the dimerization domain of λrepressor, a soluble DNA-binding protein of bacteriophage (Hu et al, Science 250:1400, 1990), and in the preparation of a dimeric form of MalE, a maltose binding protein of E. coli that is exported into the periplasmic space (Blondel and Bedoulle, Protein Engineering 4:457, 1991).

SUMMARY OF THE INVENTION

The present invention relates to a method of preparing a soluble, hetero-oligomeric mammalian polypeptide by culturing a host cell transformed or transfected with an expression vector encoding a fusion protein comprising a leucine zipper domain and a heterologous mammalian polypeptide. Preferably, the heterologous mammalian polypeptide comprises subunit polypeptides that function cooperatively to bind the ligand. In one embodiment, the heterologous mammalian polypeptide comprises ectodomains of IL-2 receptors alpha and beta.

BRIEF DESCRIPTION OF THE DRAWINGS

FIG. 1. Helical wheel representations of FIG. 1A discloses, the heterotrimeric association of the coiled-coil (cc) sequences fused to the alpha and beta IL-2 receptor (R) ectodomains in the alpha/beta cc complex (arrows indicate potential electrostatic interactions) and FIG. 1B discloses, the homotrimeric association of the coiled-coil sequences fused to the IL-2R alpha ectodomain in the alpha cc complex.

Figure 4:
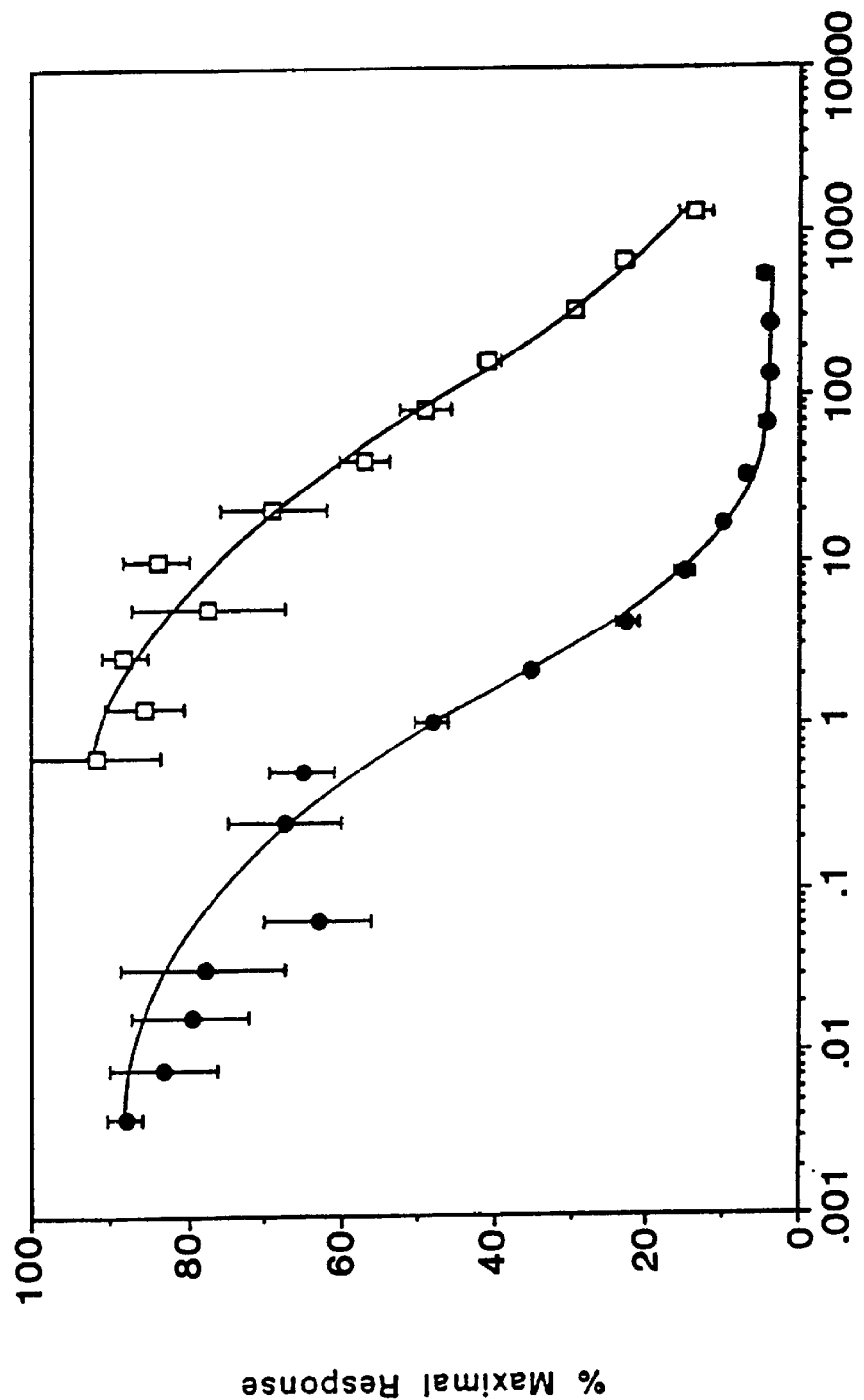

FIG. 4. Neutralization of IL-2 bioactivity by the alpha/beta cc complex (solid circles) and the alpha cc complex (open squares) in the human HPBL bioassay. The assay was performed as described (8) in the presence of an EC$_{50}$ of IL-2 (10 pM). Each data point is the mean of triplicate determinations with standard deviation. Maximum response to 10 pM, IL-2 was 6055 cpm with a background response of 88 cpm in wells where no IL-2 was added.

FIG. 5. Sedimentation coefficient distribution (32) of the alpha/beta cc complex at a loading concentration of 0.52 mg/ml (uninterrupted line), 0.25 mg/ml (dashed line) and 0.08 mg/ml (dotted line). Aggregated material is noted from 8–12 s at 0.52 mg/ml. Trailing edge from 1–2 s for all loading concentrations is indicative of some smaller material. Integration of the major peak at each loading concentration indicates that the trimeric complex represents 80–95 % of migrating species.

DETAILED DESCRIPTION OF THE INVENTION

The present invention relates to a method of preparing a soluble hetero-oligomeric mammalian polypeptide (or protein) by culturing a host cell transformed or transfected with an expression vector encoding a fusion protein comprising a leucine zipper domain and a heterologous mammalian protein. Preferably, the heterologous mammalian protein comprises subunit proteins that function cooperatively to bind the ligand. In one embodiment, the heterologous mammalian protein comprises the IL-2 alpha and beta receptor ectodomains. Cooperative binding can occur with different receptors that act together to bind a ligand (such as IL-2), for example. Exemplary mammalian transmembrane proteins include members of the tumor necrosis factor/nerve growth factor receptor (TNFR/NGFR) family (Farrah and Smith, Nature 358:26, 1992; Goodwin et al., Cell 73:447; 1993), which includes CD40 Ligand (CD40-L), CD27 Ligand (CD27-L), OX40 Ligand (OX40-L), and TNF. Structural studies of certain members of this family of proteins indicate that they form homotrimers. The inventive method will also be useful for other members of this family.

Additionally, many other mammalian transmembrane proteins form oligomers, either hetero-oligomers or homo-oligomers, in their biologically-active form. Members of the hematopoietin receptor family (Cosman et al., Trends Biochem. Sci. 15:265; 1990) are exemplary of such proteins. Gearing et al. (Science 255:1434, 1992) reported the cloning of a gene encoding a protein (gpl130) that conferred high-affinity binding to both leukemia-inhibitory factor (LIF) and oncostatin M (OSM) when expressed in cells along with a low-affinity LIF receptor. Similar interactions of a low affinity receptor and a second subunit protein, resulting in a high-affinity receptor have also been proposed for other members of this family (Hayashida et al., Proc. Natl. Acad. Sci. U.S.A. 87:0655, 1990; Kitamura et al., Cell 66:1165, 1991; Tavernier et al., Cell 66:1 175, 1991; Devos et al., EMBO J. 10:2133, 1991). Soluble forms of the members of the hematopoietin receptor family will exhibit higher affinity for their cognate ligand when expressed as hetero-oligomers, or in some cases, as homo oligomers. The same will be true for other transmembrane proteins that comprise two or more subunits.

In a preferred embodiment, the heterologous mammalian protein comprises alpha and beta IL-2 receptor ectodomains. Such receptor ectodomains will also be useful in the inventive method, wherein a leucine zipper domain stabilizes the proper quaternary structure of the oligomeric cytokine or its receptor. The preferred heterologous mammalian protein comprising alpha and beta IL-2 receptor ectodomains should be useful as a therapeutic for transplant rejections (particularly acute episodes), and certain autoimmune diseases (type 1 diabetes, rheumatoid arthritis), for example. Other hetero-oligomers can find utility in areas for which they are commonly known, as set out below. As a therapeutic, the hetero-oligomers can be admixed with pharmaceutical excipients that are commonly known in the industry. For example, see U. S. Pat. Nos. 5,037,644, and 5,078,997 for examples of common excipients and formulants. Each of these patents is hereby incorporated by reference in their entireties.

Other embodiments of hetero-oligomeric forms of cytokines are prepared as shown below. A fusion protein of granulocyte-macrophage colony stimulating factor (GM-CSF) and Interleukin-3 (IL-3) has been shown to be a more potent proliferation stimulus than either factor alone or IL-3 and GM-CSF combined (U.S. Pat. Nos. 5,073,627 and 5,108,910). Fusion proteins comprising GM-CSF and IL-3 and DNA sequences encoding such fusion proteins are described in U.S. Pat. Nos. 5,073,627 and 5,108,910, respectively, both of which are incorporated by reference herein. A similar, bivalent protein composed of GM-CSF and IL-3 may be formed by the expression of these cytokines as fusion proteins comprising leucine zipper domains that preferentially form heterodimers.

Leucine Zipper Domains

Leucine zippers were originally identified in several DNA-binding proteins (Landschulz et al., Science 240: 1759, 1988). Leucine zipper domain is a term used to refer to a conserved peptide domain present in these (and other) proteins, which is responsible for dimerization of the proteins. The leucine zipper domain (also referred to herein as an oligomerizing, or oligomer-forming, domain) comprises a repetitive heptad repeat, with four or five leucine residues interspersed with other amino acids. Examples of leucine zipper domains are those found in the yeast transcription factor GCN4 and a heat-stable DNA-binding protein found in rat liver (C/EBP; Landschulz et al., Science 243:1681, 1989). Two nuclear transforming proteins, fos and jun, also exhibit leucine zipper domains, as does the gene product of the murine proto-oncogene, c-myc (Landschulz et al., Science 240:1759, 1988). The products of the nuclear oncogenes fos and jun comprise leucine zipper domains which preferentially form a heterodimer (O'Shea et al., Science 245:646, 1989; Turner and Tjian, Science 243:1689, 1989). The leucine zipper domain is necessary for biological activity (DNA binding) in these proteins. Preferred leucine zipper domains are synthetic, not naturally occurring sequences, as they can be more stable.

The fusogenic proteins of several different viruses, including paramyxovirus, coronavirus, measles virus and many retroviruses, also possess leucine zipper domains (Buckland and Wild, Nature 338:547,1989; Britton, Nature 353:394, 1991; Delwat and Mosialos, AIDS Research and Human Retroviruses 6:703, 1990). The leucine zipper domains in these fusogenic viral proteins are near the transmembrane region of the proteins; it has been suggested that the leucine zipper domains could contribute to the oligomeric structure of the fusogenic proteins. Oligomerization of fusogenic viral proteins is involved in fusion pore formation (Spruce et al, Proc. Natl. Acad. Sci.U.S.A. 88:3523, 1991). Leucine zipper domains have also been recently reported to play a role in oligomerization of heat-shock transcription factors (Rabindran et al., Science 259:230, 1993). Leucine zipper domains fold as short, parallel coiled coils. (O'Shea et al., Science 254:539; 1991) The general architecture of the parallel coiled coil has been well characterized, with a "knobs-into-holes" packing as proposed by Crick in 1953 (Acta Crystallogr. 6:689). The dimer formed by a leucine zipper domain is stabilized by the heptad repeat, designated (abcdefg)$_n$ according to the notation of McLachlan and Stewart (J. Mol. Biol. 98:293; 1975), in which residues a and d are generally hydrophobic residues, with d being a leucine, which line up on the same face of a helix. Oppositely-charged residues commonly occur at positions g and e. Thus, in a parallel coiled coil formed from two helical leucine zipper domains, the "knobs" formed by the hydrophobic side chains of the first helix are packed into the "holes" formed between the side chains of the second helix.

The leucine residues at position d contribute large hydrophobic stabilization energies, and are important for dimer formation (Krystek et al., Int. J. Peptide Res. 38:229, 1991). Lovejoy et al. recently reported the synthesis of a triple stranded alpha-helical bundle in which the helices run up-up-down (Science 259:1288, 1993). Their studies confirmed that hydrophobic stabilization energy provides the main driving force for the formation of coiled coils from helical monomers. These studies also indicate that electrostatic interactions contribute to the stoichiometry and geometry of coiled coils. Several studies have indicated that conservative amino acids may be substituted for individual leucine residues with minimal decrease in the ability to dimerize; multiple changes, however, usually result in loss of this ability (Landschulz et al., Science 243:1681, 1989; Turner and Tjian, Science 243:1689, 1989; Hu et al., Science 250:400, 1990). van Heekeren et al. reported that a number of different amino residues can be substituted for the leucine residues in the leucine zipper domain of GCN4, and further found that some GCN4 proteins containing two leucine substitutions were weakly active (Nucl. Acids Res. 20:3721, 1992). Mutation of the first and second heptadic leucines of the leucine zipper domain of the measles virus fusion protein (MVFP) did not affect syncytium formation (a measure of virally-induced cell fusion); however, mutation of all four leucine residues prevented fusion completely (Buckland et al., J. Gen. Virol. 73:1703, 1992). None of the mutations affected the ability of MVF to form a tetramer. Recently, amino acid substitutions in the a and d residues of a synthetic peptide representing the GCN4 leucine zipper domain have been found to change the oligomerization properties of the leucine zipper domain (Alber, Sixth Symposium of the Protein Society, San Diego, Calif.). When all residues at position a are changed to isoleucine, the leucine zipper still forms a parallel dimer. When, in addition to this change, all leucine residues at position d are also changed to isoleucine, the resultant peptide spontaneously forms a trimeric parallel coiled coil in solution. Substituting all amino acids at position d with isoleucine and at position a with leucine results in a peptide that tetramerizes. Peptides containing these substitutions are still referred to as leucine zipper domains since the mechanism of oligomer formation is believed to be the same as that for traditional leucine zipper domains such as those described above. However, prior to the present invention, the effect of these substitutions upon longer peptides of which the leucine zipper is but a small domain was not known, nor was it known if peptides comprising these sequences could be expressed and secreted by cells. We have found that synthetic leucine zipper domains are more stable than naturally occurring domains. For example, we synthesized two domains for the alpha and beta ectodomains. They are LEALKEK (SEQ ID NO: 1) (single letter code for amino acids) for the alpha receptor and LKAKEKE (SEQ ID NO: 2) for the beta receptor. Leucine zipper amino acid sequences can be designed using the considerations mentioned below (see Example 1).

Preparation of Gene Fragments and oligonucleotides

Oligonucleotide fragments of about 12 to about 20 nucleotides may be prepared according to methods that are known in the art, for example, by using an automated DNA synthesizer. Several such fragments may be synthesized, which encode overlapping portions of a peptide, for example, a leucine zipper domain. Due to the degeneracy of the genetic code, most amino acids are encoded by two or more different nucleotide triplets. The selection of a triplet to encode a given amino acid will depend upon the organism in which the final gene product is to be expressed among other considerations. Overlapping fragments may then be joined to form a DNA encoding a peptide of interest. A polymerase chain reaction (PCR) technique (Saiki et al., Science 239:487, 1988) may be employed to amplify gene fragments encoding all or a portion of a protein of interest, using 5' (upstream) and 3' (downstream) oligonucleotide primers derived from the known DNA sequence of the gene, or a gene encoding a related protein. An exemplary set of PCR conditions includes: one cycle at 94° C. for 2 minutes, followed by 42° C. for two minutes; 30 cycles at 72° C /for 1.5 minutes, followed by 94° C. for one minute, then 48° C. for 1 minute; and one cycle at 72° C. for seven minutes. Restriction enzyme sites can also be added to the DNA sequences of interest, in order to facilitate ligation of the resulting PCR product with a plasmid or vector, or with an additional DNA sequence or sequences. Amplified DNA sequences may be joined substantially as described in Yon and Fried (Nucleic Acids Res. 17:4895; 1989). For example, full length mouse OX40 was cloned using 5' (upstream) and 3' (downstream) oligonucleotide primers based on the published sequence of rat OX40. The upstream primer comprised a recognition site for the restriction endonuclease Spe I upstream of a sequence encoding the first six (N-terminal) amino acids of rat OX40. The downstream primer comprised a recognition site for the restriction endonuclease Spe I upstream of a sequence encoding the last five (C-terminal) amino acids of full-length OX40. The PCR product was digested with Spe I, and an approximately 800 bp fragment was isolated by gel filtration, and used in a second round of PCR reaction. The isolated fragment was ligated into Spe I cut plasmid, pBLUESCRIPT SK (registered trademark) (Stratagene Cloning Systems, La Jolla, Calif.), which had been treated with calf intestine alkaline phosphatase (CIAP) to prevent self-ligation.

In another example, a DNA encoding only the extracellular region of a transmembrane protein can be obtained by deleting DNA encoding the intracellular and transmembrane portions of the transmembrane protein. Methods to determine which residues should be deleted and for performing the actual deletions are well known in the art. For example, Smith et al. describe a soluble form of the human CD4 antigen prepared by deleting the transmembrane and intracellular portions of the CD4 antigen (Science 238:1704, 1987). Treiger et al. prepared a soluble form of an IL-2 receptor using similar methods (J. Immunol. 136:4099, 1986).

A fusion protein may be formed from an extracellular region and a protein (or portion thereof) that is known to be secreted. For example, soluble proteins comprising an extracellular domain from a membrane-bound protein and an immunoglobulin heavy chain constant region was described by Fanslow et al., J. Immunol. 149:65, 1992 and by Noelle et al., Proc. Natl. Acad. Sci. U.S.A. 89:6550, 1992. The extracellular domain of the murine T lymphocyte antigen CD8 has also been utilized to form soluble fusion proteins (Hollenbaugh et al., EMBO J. 11:4313, 1992).

Preparation of Fusion Proteins

Fusion proteins are polypeptides that comprise two or more regions derived from different or heterologous, proteins or peptides. Fusion proteins are prepared using conventional techniques of enzyme cutting and ligation of fragments from desired sequences. PCR techniques employing synthetic oligonucleotides may be used to prepare and/or amplify the desired fragments. Overlapping synthetic oligonucleotides representing the desired sequences can also be used to prepare DNA constructs encoding fusion proteins. Fusion proteins can comprise several sequences, including a leader (or signal peptide) sequence, linker sequence, a leucine zipper sequence, or other oligomer-forming sequences, and sequences encoding highly antigenic moieties that provide a means for facile purification or rapid detection of a fusion protein.

Signal peptides facilitate secretion of proteins from cells. An exemplary signal peptide is the amino terminal 25 amino acids of the leader sequence of murine interleukin-7 (IL-7; Namen et al, Nature 333:571; 1988). Other signal peptides may also be employed. Furthermore, certain nucleotides in the IL-7 leader sequence can be altered without altering the amino acid sequence. Additionally, amino acid changes that do not affect the ability of the IL-7 sequence to act as a leader sequence can be made.

The FLAG® (a registered trademark) octapeptide (Hopp et al., Bio/Technology 6:1204, 1988) does not alter the biological activity of fusion proteins is highly antigenic and provides an epitope reversibly bound by a specific monoclonal antibody, enabling rapid detection and facile purification of the expressed fusion protein. The FLAG® sequence is also specifically cleaved by bovine mucosal enterokinase at the residue immediately following the Asp-Lys pairing. Fusion proteins capped with this peptide may also be resistant to intracellular degradation in E. coli. A murine monoclonal antibody that binds the FLAG® sequence has been deposited with the ATCC under Accession number HB 9259. Methods of using the antibody in purification of fusion proteins comprising the FLAG® sequence are described in U.S. Pat. No. 5,011,912, which is incorporated by reference herein.

A protein of interest may be linked directly to another protein to form a fusion protein. Alternatively, the proteins may be separated by a "linker" amino acid sequence of a length sufficient to ensure that the proteins form proper secondary and tertiary structures. Suitable linker sequences (1) will adopt a flexible extended conformation, (2) will not exhibit a propensity for developing ordered secondary structure which could interact with the functional domains of fusion proteins, and (3) will have minimal hydrophobic or charged character which could promote interaction with the functional protein domains. Typical surface amino acids in flexible protein regions include Gly, Asn and Ser. Virtually any permutation of amino acid sequences containing Gly, Asn and Ser would be expected to satisfy the above criteria for a linker sequence. Other near neutral amino acids, such as Thr and Ala, may also be used in the linker sequence. The length of the linker sequence may vary without significantly affecting the biological activity of the fusion protein. Linker sequences are unnecessary where the proteins being fused have non-essential N- or C-terminal amino acid regions which can be used to separate the functional domains and prevent stearic interference. Exemplary linker sequences are described in U.S. Pat. Nos. 5,073,627 and 5,108,910, the disclosures of which are incorporated by reference herein.

When an oligomeric fusion protein is formed from the extracellular portion of a transmembrane protein, a DNA sequence encoding an oligomer-forming domain, such as a leucine zipper domain, is fused to a DNA sequence encoding the extracellular region of the transmembrane protein. The members of the fusion protein are joined such that the oligomer-forming domain of the fusion protein is located in the same orientation relative to the fusion protein as the transmembrane and intracytoplasmic regions of the native transmembrane protein. An oligomeric fusion protein will be stabilized by the coiled-coil interaction of the leucine zipper domain. Thus, in one example, a fusion protein comprising an extracellular region derived from a ligand for CD40 (CD40-L), a type II transmembrane protein described in WO 94/10308, the disclosure of which is incorporated by reference herein, the oligomer-forming domain, a leucine zipper sequence, is fused to the amino-proximal end of the extracellular region. In a fusion protein derived from a type I transmembrane protein, the oligomer-forming domain would be fused to the carboxy-proximal end of the extracellular region of the type I transmembrane protein. Other transmembrane proteins traverse the cell membrane more than once. Such transmembrane proteins will have two or more different extracellular regions. Soluble oligomeric fusion proteins may also be prepared from two or more of such different extracellular regions from the same transmembrane protein.

Oligomeric forms of proteins that occur naturally in soluble form may also be prepared. In such cases, the oligomer-forming domain is joined to the soluble protein such that formation of an oligomer follows the conformation of the biologically active, soluble protein. Furthermore, either homo-oligomeric proteins or hetero-oligomeric proteins can be prepared, depending upon the whether the oligomerizing domain(s) of the fusion protein preferentially form hetero-oligomers or homo-oligomers.

Expression Vectors

Recombinant expression vectors for expression of a fusion protein comprising an oligomer-forming domain and a heterologous mammalian protein by recombinant DNA techniques, include a DNA sequence comprising a synthetic or CDNA-derived DNA fragment encoding an oligomer-forming domain, linked in frame to a DNA fragment encoding the heterologous protein. These DNA fragments are operably linked to suitable transcription and/or translational regulatory nucleotide sequences, such as those derived from a mammalian, microbial, viral, or insect gene. Examples of regulatory sequences include sequences having a regulatory role in gene expression (e.g., a transcription promoter or enhancer), an operator sequence to control transcription, a sequence encoding an mRNA ribosomal binding site, polyadenylation site, splice donor and acceptor sites, and appropriate sequences which control transcription, translation, initiation and termination. In addition, sequences encoding signal peptides can be incorporated into expression vectors. For example, a DNA sequence for a signal peptide (secretory leader) may be operably linked to a DNA encoding a fusion protein comprising an oligomer-forming domain and a heterologous mammalian protein. The signal peptide is expressed as a part of a precursor amino acid sequence; the signal peptide enables improved extracellular secretion of translated fusion polypeptide by a host cell.

Nucleotide sequences are operably linked when the regulatory sequence functionally relates to the DNA encoding the fusion protein. Thus, a promoter nucleotide sequence is operably linked to a DNA encoding a fusion protein if the promoter nucleotide sequence controls the transcription of the DNA encoding the fusion protein. Still further, a ribosome binding site may be operably linked to a sequence for a fusion protein if the ribosome binding site is positioned within the vector to encourage translation.

Transcription and translational control sequences for mammalian host cell expression vectors may be excised from viral genomes. For example, commonly used mammalian cell promoter sequences and enhancer sequences are derived from Polyoma virus, Adenovirus 2, Simian Virus 40 (SV40), and human cytomegalovirus. DNA sequences derived from the SV40 viral genome, for example, the SV40 origin, early and late promoters, enhancer, splice, and polyadenylation sites may be used to provide the other genetic elements required for expression of a structural gene sequence in a mammalian host cell. Viral early and late promoters are particularly useful because both are easily obtained from a viral genome as a fragment which may also contain a viral origin of replication (Fiers et al., Nature 273:113, 1978). Smaller or larger SV40 fragments may also be used, provided the approximately 250 bp sequence extending from the Hind III site toward the Bgl I site located in the SV40 viral origin of replication site is included.

Exemplary mammalian expression vectors can be constructed as disclosed by Okayama and Berg (Mol. Cell. Biol. 3:280, 1983). A useful high expression vector, PMLSV N1/N4, described by Cosman et al., Nature 312:768, 1984 has been deposited as ATCC 39890. Additional useful mammalian expression vectors are described in EP 0367566, incorporated by reference herein. For expression of a type II protein extracellular region, such as OX40-L, a heterologous signal sequence may be added, such as the signal sequence for interleukin-7 (IL-7) described in U.S. Pat. No. 4,965,195, or the signal sequence for interleukin-2 receptor. Another exemplary vector is pDC406, which includes regulatory sequences derived from SV40, human immunodeficiency virus (HIV), and Epstein-Barr virus (EBV).

Expression vectors transfected into prokaryotic host cells generally comprise one or more phenotypic selectable markers. A phenotypic selectable marker is, for example, a gene encoding a protein that confers antibiotic resistance or that supplies an autotrophic requirement, and an origin of replication recognized by the host to ensure amplification within the host. Other useful expression vectors for prokaryotic host cells include a selectable marker of bacterial origin derived from commercially available plasmids. This selectable marker can comprise genetic elements of the cloning vector pBR322 (ATCC 37017). pBR322 contains genes for ampicillin and tetracycline resistance and thus provides simple means for identifying transformed cells. The pBR322 "backbone" sections are combined with an appropriate promoter and an OX40-L DNA sequence. Other commercially vectors include, for example, pKK223-(Pharmacia Fine Chemicals, Uppsala, Sweden) and pGEM I (Promega Biotec, Madison, Wis., USA).

Promoter sequences are commonly used for recombinant prokaryotic host cell expression vectors. Common promoter sequences include beta-lactamase (penicillinase), lactose promoter system (Chang et al., Nature 275:615, 1978; and Goeddel et al., Nature 281:544, 1979), tryptophan (trp) promoter system (Goeddel et al., Nucl. Acids Res. 8:4057, 1980; and EP 36776) and tac promoter (Maniatis, Molecular Cloning: A Laboratory Manual, Cold Spring Harbor Laboratory, p. 412, 1982). A particularly useful prokaryotic host cell expression system employs a phage lambda PL promoter and a cI857ts thermolabile repressor sequence. Plasmid vectors available from the American Type Culture Collection which incorporate derivatives of the lambda PL promoter include plasmid pHUB2 (resident in *E. coli* strain JMB9 (ATCC 37092)) and pPLc28 (resident in *E. coli* RR1 (ATCC 53082)).

Host Cells

Suitable host cells for expression of a fusion protein comprising an oligomer-forming domain and a heterologous mammalian protein include prokaryotes and higher eukaryotic cells. Prokaryotes include gram negative or gram positive organisms, for example, *E. coli*, Bacilli. Suitable prokaryotic host cells for transformation include, for example, *E. coli, Bacillus subtilis, Salmonella typhimurium* and various other species within the genera Pseudomonas, Streptomyces, and Staphylococcus. Higher eukaryotic cells include established cell lines of mammalian or insect origin. Cell-free translation systems could also be employed to produce a fusion protein comprising an oligomer-forming domain and a heterologous mammalian protein using an RNA derived from DNA constructs disclosed herein.

In a prokaryolic host cell, such as *E. coli*, a fusion protein may include an N-terminal methionine residue to facilitate expression of the recombinant polypeptide in the prokaryotic host cell. The N-terminal Met may be cleaved from the expressed recombinant fusion protein. Prokaryotic host cells may be used for expression of fusion proteins that do not require extensive proteolytic or disulfide processing.

Appropriate cloning and expression vectors for use with bacterial, fungal, yeast, and mammalian cellular hosts are described, for example, in Pouwels et al. Cloning Vectors: A Laboratory Manual, Elsevier, N.Y., (1985). An expression vector carrying the recombinant fusion protein DNA is transfected or transformed into a substantially homogeneous culture of a suitable host microorganism or mammalian cell line according to methods that are known in the art to form transfected or transformed host cells that express the fusion protein. Expressed fusion protein will be located within the host cell and/or secreted into culture supernatant fluid, depending upon the nature of the host cell and the gene construct inserted into the host cell. A fusion protein comprising an oligomer-forming domain and a heterologous mammalian protein may be expressed in yeast host cells, preferably from the Saccharomyces genus (e.g., *S. cerevisiae*). Other genera of yeast, such as Pichia or Kluyveromyces, may also be employed. Yeast vectors will often contain an origin of replication sequence from a 2 micron yeast plasmid, an autonomously replicating sequence (ARS), a promoter region, sequences for polyadenylation, and sequences for transcription termination. Preferably, yeast vectors include an origin of replication sequence and selectable marker. Suitable promoter sequences for yeast vectors include promoters for metallothionein, 3-phosphoglycerate kinase (Hitzeman et al., J. Biol. Chem. 255:2073, 1980) or other glycolytic enzymes (Hess et al., J. Adv. Enzyme Reg. 7:149, 1968: and Holland et al. Biochem. 17:4900, 1978), such as enolase, glyceraldehyde-3-phosphate dehydrogenase, hexokinase, pyruvate decarboxylase, phosphofructokinase, glucose-6-phosphate isomerase, 3-phosphoglycealate mutase, pyruvate kinase, triosephosphate isomerase, phosphoglucose isomerase, and glucokinase. Other suitable vectors and promoters for use in yeast expression are further described in Hitzeman, EP 73657.

Yeast vectors can be assembled, for example, using DNA sequences from pBR322 for selection and replication in *E.*

*coli* (Amp$^r$ gene and origin of replication). Other yeast DNA sequences that can be included in a yeast expression construct include a glucose-repressible ADH2 promoter and alpha-factor secretion leader. The ADH2 promoter has been described by Russell et al. (J. Biol. Chem. 258:2674, 1982) and Beier et al. (Nature 300:724, 1982). The yeast alpha-factor leader sequence directs secretion of heterologous polypeptides. The alpha-factor leader sequence is often inserted between the promoter sequence and the structural gene sequence. See, e.g., Kurjan et al., Cell 300:933, 1982 and Bitter et al., Proc. Natl. Acad. Sci. U.S.A. 81:5330, 1984. Other leader sequences suitable for facilitating secretion of recombinant polypeptides from yeast hosts are known to those of skill in the art. A leader sequence may be modified near its 3' end to contain one or more restriction sites. This will facilitate fusion of the leader sequence to the structural gene.

Yeast transformation protocols are known to those of skill in the art. One such protocol is described by Hinnen et al., Proc. Natl. Acad. Sci. U.S.A. 75:1929, 1978. For example, one can select for Trp+ transformants in a selective medium, wherein the selective medium consists of 0.67% yeast nitrogen base, 0.5% casamino acids, 2% glucose, 10 microgram/ml adenine and 20 micrograms/ml uracil. Yeast host cells transformed by vectors containing ADH2 promoter sequence may be grown for inducing expression in a "rich" medium. An example of a rich medium is one consisting of 1% yeast extract, 2% peptone, and 1 % glucose supplemented with 80 micrograms/ml adenine and 80 microgram/ml uracil. Derepression of the ADH2 promoter occurs when glucose is exhausted from the medium.

Mammalian or insect host cell culture systems could also be employed to express recombinant fusion protein. Examples of suitable mammalian host cell lines include the cos-7 line of monkey kidney cells (ATCC CRL 1651; Gluzman et al., Cell 23:175, 1981), L cells, C127 cells, 3T3 cells (ATCC CRL 163), Chinese hamster ovary (CHO) cells, HeLa cells, BHK (ATCC CRL 10) cell lines, and CV-1/EBNA cells (ATCC CRL 10478). The CV-1/EBNA cell line was derived by transfection of the CV-1 cell line with a gene encoding Epstein-Barr virus nuclear antigen-1 (EBNA-1) and constitutively express EBNA-1 driven from human CMV immediate-early enhancer/promoter. An EBNA-I gene allows for episomal replication of expression vectors that contain the EBV origin of replication. Insect cell lines, such as those from *Spodoptera frugiperda* or *Autographa californica*, can be employed in cloning or producing the protein. See Summers and Smith (1987) or WO 94/01547 which are hereby incorporated by reference in their entireties.

Protein Purification

Purified soluble fusion proteins are prepared by culturing suitable host/vector systems to express the recombinant soluble fusion proteins, which are their purified from culture media or cell extracts, using standard methods of protein purification that are optimized for each individual soluble fusion protein.

For example, supernatants from systems which secrete recombinant protein into culture media are clarified, and concentrated using a commercially available protein concentration filter, for example, an Amicon or Millipore Pellicon ultrafiltration unit. Following the concentration step, the concentrate can be applied to a suitable purification matrix. Suitable matrices include those useful in affinity chromatography. For example, a suitable affinity matrix can comprise a cognate protein to which the fusion protein binds, or a lectin or antibody molecule which binds the fusion protein, bound to a suitable support.

Alternatively, an ion exchange resin can be employed, for example, an anion exchange resin comprising a matrix or substrate having pendant diethylaminoethyl (DEAE) groups, or other suitable anion exchangers. The matrices can be acrylamide, agarose, dextran, cellulose or other types commonly employed in protein purification. Alternatively, a cation exchange step can be employed. Suitable cation exchangers include various insoluble matrices comprising sulfopropyl or carboxymethyl groups.

One or more reversed-phase high performance liquid chromatography (RP-HPLC) steps employing hydrophobic RP-HPLC media, e.g., silica gel having pendant methyl or other aliphatic groups, can be employed to further purify a soluble fusion protein. Size exclusion chromatography will also be useful in purifying soluble fusion proteins. Additionally, hydrophobic supports can also be used under low pressure conditions: an exemplary medium is phenyl-sepharose. Some or all of the foregoing purification steps, in various combinations, can also be employed to provide homogeneous recombinant protein.

Biological Activity

Biological activity or recombinant, soluble fusion proteins is mediated by binding of the recombinant, soluble fusion protein to a cognate molecule. A cognate molecule is defined as a molecule which binds the recombinant soluble fusion protein in a non-covalent interaction based upon the proper conformation of the recombinant soluble fusion protein and the cognate molecule. For example, for a recombinant soluble fusion protein comprising an extracellular region of a receptor, the cognate molecule comprises a ligand which binds the extracellular region of the receptor. Conversely, for a recombinant soluble fusion protein comprising a ligand, the cognate molecule comprises a receptor (or binding protein) which binds the ligand.

Binding of a recombinant fusion protein to a cognate molecule is a marker for biological activity. Such binding activity may be determined, for example, by competition for binding to the binding domain of the cognate molecule (i.e. competitive binding assays). One configuration of a competitive binding assay for a recombinant soluble fusion protein comprising a ligand uses a radiolabeled, solubie receptor, and intact cells expressing a native form of the ligand. Similarly, a competitive assay for a recombinant soluble fusion protein comprising a receptor uses a radiolabeled, soluble ligand, and intact cells expressing a native form of the receptor. Instead of intact cells expressing a native form of the cognate molecule, one could substitute purified cognate molecule bound to a solid phase. Competitive binding assays can be performed using standard methodology. Qualitative or semi-quantitative results can be obtained by competitive autoradiographic plate binding assays, or fluorescence activated cell sorting, or Scatchard plots may be utilized to generate quantitative results.

Biological activity may also be measured using bioassays that are known in the art, such as a cell proliferation assay. The type of cell proliferation assay used will depend upon the recombinant soluble fusion protein. A bioassay for a recombinant soluble fusion protein that in its native form acts upon T cells will utilize purified T cells obtained by methods that are known in the art. Such bioassays include co-stimulation assays in which the purified T cells are incubated in the presence of the recombinant soluble fusion protein and a suboptimal level of a mitogen such as Con A or PHA. Similarly, purified B cells will be used for a recombinant soluble fusion protein that in its native form acts upon B cells. Other types of cells may also be selected based upon the cell type upon which the native form of the recombinant soluble fusion protein acts. Proliferation is determined by measuring the incorporation of a radiolabeled substance, such as 3H thymidine, according to standard methods.

Yet another type of assay for determining biological activity is induction of secretion of secondary molecules. For example, certain proteins induce secretion of cytokines by T cells. T cells are purified and stimulated with a recombinant soluble fusion protein under the conditions required to induce cytokine secretion for example, in the presence of a comitogen. Induction of cytokine secretion is determined by bioassay, measuring the proliferation of a cytokine dependent cell line. Similarly, induction of immunoglobulin secretion is determined by measuring the amount of immunoglobulin secreted by purified B cells stimulated with a recombinant soluble fusion protein that acts on B cells in its native form, using a qualitative (or semi-quantitative) assay such as an enzyme immunoassay.

The relevant disclosures of all references cited herein are specifically incorporated by reference. The following examples are offered by way of illustration, and not by way of limitation.

EXAMPLES

Example 1

This example refers to studies performed in various citations listed below. Each reference is hereby incorporated by reference in its entirety.

The high affinity Interleukin-2 receptor is composed of at least three cell surface proteins (alpha, beta and gamma subunits) each of which is independently capable of ligand binding. Physiologically, these subunits cooperate to form dimeric and trimeric complexes that efficiently capture IL-2 and transmit the signal across the membrane. The knowledge of how each subunit functions with respect to ligand capture, signal transmission and internalization is essential for the development of ligand based IL-2 agonists and antagonists as well as receptor related therapeutic and diagnostic reagents. Only one of the subunits (p55 or d chain) is capable of interacting with ligand in solution in a manner that resembles cell surface binding. In order to generate soluble multimeric complexes of the IL-2 receptor subunits that may bind ligand in solution in a fashion that mimics the same receptor complexes on the cell surface, we have added recognition sequences (coiled-coil heptad repeats) to the ectodomains of the individual receptors. Here we describe the expression and characterization a prototype IL-2 beta receptor ectodomain/coiled-coil fusion protein and demonstrate that this is a feasible approach to the preparation of cytokine receptor solution complexes.

Interleukin-2 (IL-2) is a 15.5 kDa protein that belongs to a growing family of structurally related cytokines (Bazan, 1989; Parry et al., 1988; Parry et al., 1991). It functions as a regulator of T-cell proliferation (Smith, 1988) and natural killer cell activity (Caligiuri et al., 1990). For IL-2, structure-function analysis has proven particularly challenging because of the multimeric nature of the IL-2 receptor (IL-2R) (Takeshita et al., 1992; Wang and Smith, 1987). The biologically significant high affinity binding site results from the non-covalent interaction of three cell surface proteins, each of which is capable of independently binding IL-2 with much lower affinity. The 55 kDa alpha-subunit (p55) binds IL-2 with a dissociation constant ($K_d$) of $1 \times 10^{-8}$ molar (Sabe et al., 1984) and is known as the low affinity form of the receptor.

The larger 75 kDa beta-subunit (p75), originally reported as having a Kd=$1 \times 10^{-9}$ molar, was simultaneously identified on human and gibbon ape cell lines by several laboratories (Dukovich et al., 1987; Sharon et al., 1987; Teshigawara et al., 1987; Tsudo et al., 1986). When DNA clones for both the p55 and p75 subunits (Hatakeyama et al., 1989; Nikaido et al., 1984) were simultaneously transfected into non-lymphoid cell lines, however, a functional high affinity receptor could not be detected. The speculation that additional proteins may be involved in ligand binding was confined by the identification of a third subunit (p64 or gamma) detectable in the ligand-bound form of the receptor in lymphoid cell lines (Takeshita et al., 1992a; Takeshita et al., 1992b). In the presence of IL-2, this protein associates with p75 and is required to generate both the intermediate ($K_d$ approximately 1 nmolar) and high ($K_d$ approximately 10 pmolar) affinity sites. Cooperative binding of IL-2 by these three proteins ultimately results in cross-linking of the beta- and gamma-subunits and signaling via association of their cytoplasmic domains (Nakamura et al., 1994). Recent reports indicating that the IL-2R gamma- subunit is also shared by the IL-4 and IL-7 receptors (Russell et al., 1993; Kondo et al., 1993; Noguchi et al., 1993a) help explain the observation that point mutations in this protein can result in severe X-linked immunodeficiency (Noguchi et al., 1993b). Both beta- and gamma-subunits participate in the formation of the IL-15 receptor (Giri et al., 1994).

Both p75 and p64 (but not p55) are members of the recently recognized hematopoietic receptor superfamily, that includes receptors for IL-2, IL-3, IL-4, IL-5, IL-6, IL-7, granulocyte/macrophage colony stimulating factor (GM-CSF), erythropoietin (EPO), growth hormone (HGH), and prolactin (Bazan, 1989; Bazan, 1990; Cosman, 1993; Cosman et al., 1990; Minami et al., 1993). A characteristic of this receptor family is that receptor triggering results from ligand mediated subunit crosslinking, forming either a homodimer, as was determined for the human growth hormone receptor (HGHR) (De Vos et al., 1992), or a heterodimer as apparently occurs for several other cytokine receptors (Cosman, 1993). The high affinity IL-2R, however, appeals to function in a manner analogous to the ciliary neurotrophic factor receptor (CTNFR) in which three different receptor subunits participate (Stahl and Yancopoulos, 1993). Nevertheless, heterodimers of IL-2R subunits serve physiologically important roles. We have previously determined that the p55/p75 (alpha/beta) heterodimer complex exists preformed on the surface of activated T-cells and serves to capture ligand (Landgraf et al., 1992). This observation was in accord with theoretical analyses of ligand binding data (Goldstein et al., 1992). In addition, the p75/p64 (beta/gamma) heterodimer that apparently forms the signaling complex in the presence of IL-2 exists on the majority of NK cells in the absence of the alpha-subunit (Caligiuri et al., 1990). Therefore the multimeric IL-2R may exist in several physiologically functional forms. In order to study the structural and ligand binding properties of these complexes in solution, we evaluated the addition of specific molecular recognition sequences to the receptor subunit ectodomains as a means of generating stable complexes that retain their ligand binding properties.

One recognition element that promises to be particularly suitable for this purpose is the coiled-coil heptad repeat. Although the coiled-coil interaction was first described 40 years ago by Crick (Crick, 1953) and has since been studied in detail for several years by Hodges as the structural element present in tropomyosin (Hodges, 1979; Hodges et al., 1981; Hodges et al., 1972; Hodges et al., 1990; Talbot and Hodges, 1982; Zhou et al., 1992; Zhou et al., 1992; Zhou et al., 1993; Zhu et al., 1993; Zhu et al., 1992), the broader biologic significance of this motif was not appreciated until the interaction was "rediscovered" as a critical recognition sequence mediating association of a family of dimeric DNA binding proteins (Landschulz et al., 1988). It is now recognized that coiled-coil molecular recognition is a common feature in many macromolecular complexes, the structural features of which have been extensively investigated (for reviews See Alber, 1992; Cohen and Parry, 1990).

Here, we report the design, expression and characterization of a prototype IL-2R complex generated from the fusion of coiled-coil heptad repeats to the beta-subunit ectodomain of the IL-2 receptor and demonstrate the feasibility of this approach for directed, stable macromolecular complexation.

Insect cell culture. Insect *Spodoptera frugiperda* (Sf9) cells were used for generating high titer recombinant virus, and were cultured at 27° C. in 100 ml spinner flasks as previously described (Summers and Smith, 1987). Grace's insect cell culture media was purchased from GIBCO/BRL. Supplemental yeastolate and lactalbumin hydrolysate were obtained from DIFCO. Trichopluscia (High Five™) cells (Invitrogen), were used to express the recombinant protein and were grown as monolayer cultures at 27° C. in serum-free Ex-cell 400 media (JRH Bioscience). High Five cells were gently lifted by pipette action for routine passing.

Preparation and isolation of recombinant virus. Baculovirus expression vector, pBlueBac II (Invitrogen, Carlsbad, Calif.), was used in this study. To express the IL-2R beta ectodomain, the IL-2R beta DNA was ligated directly into the BamH I site of pBlueBac II as described elsewhere (Sana et al., 1994). This vector contains the beta-galactosidase gene, greatly facilitating the identification of recombinant virus in a plaque assay. To express the IL-2R beta fusion protein, synthetic oligonucleotides encoding the coiled-coil sequence were ligated to the 3' end of IL-2R beta DNA. To simplify the cloning procedure, the fusion gene was constructed in a smaller vector, pUC-19, before being inserted in the BamH I site of pBlueBac II [Two double stranded cassettes each encoding approximately one half of the required sequence were cloned directionally into the bacterial vector pUC 19. The first cassette was cloned into the parent vector in the BamH I site. This sequence contained unique restriction sites (Xho I and BstB I) allowing the insertion of the second cassette to give heptad vector. Directional cloning of the p75 ectodomain (Dsa I sites with different overhangs) provided the DNA enccoding the desired fusion protein in pUC 19 (IL-2R beta). Removal of this sequence (BamH I, Nhe I) and subcloning into the baculovirus vector pBlueBac II (Invitrogen) allowed expression in insect cells]. Due to the length of coiled-coil coding sequence, two large double stranded synthetic oligonucleotide cassettes (prepared by annealing ion exchange-purified oligonucleotides) were prepared, each encoding approximately one half of the required seven heptad repeats. In addition, 5' and 3' restriction sites (Dsa I and BamH I) were added allowing both the insertion of the IL-2RB ectodomain gene into pUC 19 and cloning of the completed construct into the baculovirus expression vector. The codon usage of the first cassette was chosen so as to incorporate unique restriction sites (Xho I and Bst B1) in the middle of the sequence allowing easy insertion of the second cassette. The correct orientation and sequence of the IL-2R beta was verified by restriction enzyme digestion and by dideoxy sequencing. To generate recombinant virus, 2×10⁶ Sf9 cells were co-transfected with 1 µg of linearized *Autographa californica* Nuclear Polyhedrosis Virus (AcNPV) DNA (Invitrogen), and 5 µg of baculovirus expression plasmid, using the liposome transfection technique according to the manufacturer's instruction. Putative recombinant plaques were visually identified by the blue color, six days post-transfection. Following one to two rounds of plaque purification, several putative recombinant plaques were isolated, verified as free of wild type contamination and stored at −20° C. Titers of recombinant virus were then amplified to 2–5×10⁸ plaque forming units (pfu)/ml.

Large-scale production of recombinant protein. High Five™ insect cells were chosen for large-scale production of recombinant proteins. To determine the time course of recombinant protein expression, a monolayer of 2×10⁷ High Five™ cells in T-162 culture flasks were infected with high titer recombinant virus employing a multiplicity of infection (MOI) of 10. At specific intervals following infection, 1 ml of culture supernatant was collected and the proteins were precipitated with 72% trichloroacetic acid and 0.15% sodium deoxycholate. After dissolving 200 µl of sample buffer, the samples were analyzed by SDS/PAGE (15% gel) and the gel was stained with Coomassie Blue R-250. Large scale infections were accomplished in 20–40 T-162 culture flasks containing 2–3×10⁷ monolayer cultured High Five™ cells. Each flask was infected with high titer recombinant virus stock at a MOI of 10. Culture medium was replaced after 2 hrs with 20 ml of fresh Ex-cell 400 serum free medium. Cell-free culture supernatants were harvested 72 hr post-infection by removing the cells at 1000 rpm for 10 min and concentrating 10–20 fold at 4° C. in an Amicon P20 concentrator (Mr=10,000 cut-off membrane). The concentrated supernatant was centrifuged at 3000 rpm (15 min at 4° C.) and then filtered through a 0.2 µm membrane prior to purification.

Affinity purification of recombinant protein. IL-2 R alpha affinity can be achieved via a Glu-Glu tag as described in Johnson et al. (1993). IL-2R beta recombinant protein was purified using an IL-2 affinity column as described elsewhere (Sana et al., 1994). One-step affinity purification of IL-2RB fusion protein complex was also achieved using an IL-2 affinity column in a similar fashion. Briefly, concentrated culture supernatants were loaded onto the IL-2 affinity columns and incubated overnight at 4° C. and then washed with cold PBS until $A_{280}$ values of the eluate remained <0.01 AU. IL-2R beta protein was then eluted with 0.2M acetic acid containing 0.2M sodium chloride. The eluate was dialyzed against two changes of PBS followed by concentration in a Centriprep 10 spin column (Amicon).

Protein purity and sequence analysis. Protein purity was verified by SDS-PAGE and reverse phase HPLC on a Waters 850 system using a Dynamax 300A C-18 RP column (Rainin). Proteins were quantitated by U.V. absorption spectroscopy (calculated IL-2R beta ectodomain molar extinction coefficient=$6.07 \times 10^4$ Liter mol$^{-1}$ cm$^1$ in 6M Gdm HCl (Johnson, 1990)). One hundred pmoles of protein were submitted for N-terminal sequencing.

Gel filtration HPLC and analytical ultracentrifugation. Gel filtration HPLC was performed using a Hewlett-Packard 1090M HPLC system equipped with a diode array detector and a TSK-G3000SWXL size exclusion column (Nest Group) calibrated with protein gel filtration calibration standards (MW-GF-200, Sigma). Proteins were dissolved in PBS and eluted in 20 mM NaPO$_4$, pH 7.0, 100 mM KCl.

Analytical ultracentrifugation analysis was carried out on a Beckman XL-A analytical ultracentrifuge equipped with Rayleigh interference optics (Laue et al., 1994). Short column sedimentation equilibrium (Yphantis, 1960) was conducted as described previously (Laue, 1992) using 12 mm-thick, short column Kel-F centerpieces, sapphire windows and a 4-hole titanium rotor. Samples were examined in 20 mM NaPO$_4$ (pH 7.0) containing 100 mM KCl and data were acquired from at least three different rotor speeds from at least three different sample concentrations for each. These data were analyzed by nonlinear least squares methods (Johnson, et al., 1981) and interpreted as previously described (Laue et al., 1992) using a partial specific volume of 0.72 ml/g and a buffer density of 1.005 g/ml. The partial specific volume was calculated using a core protein molecular weight of 30,447 having a partial specific volume of 0.74 ml/g and estimating the carbohydrate molecular weight as 8400 g/mol and assuming a partial specific volume of 0.63 ml/g (Shire, 1992). Sedimentation velocity was conducted using the same rotor at 20° C. and 48,000 rpm using interference optics and 12 mm-thick, charcoal-filled centerpieces and sapphire windows. Sedimentation coefficients were determined from the time derivative of the concentration profile as described by Stafford (Stafford, 1992) and corrected to standard conditions (Laue et al., 1992).

Circular dichroism. Far ultraviolet circular dichroism (CD) spectra for IL-2Rbx and IL-2R beta were collected on a Jobin Yvon Mark V circular dichrograph. Measurements were obtained in a 0.1 cm cell at a protein concentration of 40–100 µg/ml in NaPO$_4$ buffer (20 mM, pH 7.0 containing 100 mM KCl). An average of 30 scans were performed and a buffer blank was subtracted. Deconvolution of the resulting spectra was carried out according to Perczel (Perczel et al., 1991).

Competitive receptor binding assays. Competitive receptor binding assays were adapted from our competitive ligand binding assay (Landgraf et al., 1992) as previously described (Sana et al., 1994). Briefly, the YT-2C2 cell line (Teshigawara et al., 1987) was used in a competition assay with recombinant IL-2 receptor proteins and $^{125}$I-recombinant IL-2 (rIL-2). Competitor proteins (either an rIL-2 control or IL-2R derivatives) were serially diluted in internalization inhibitor buffer (15 nM NaN$_3$, 50 nM 2-deoxyglucose, 0.1% BSA, in PBS, pH 7.4). $^{125}$I-rIL-2 in 150 µl of solution containing competitors was overlaid onto 0.2 ml silicone/paraffin oil (80:20) in 500 µl binding tubes. 50 µl of cell suspension (5×10$^7$ cells/ml) in internalization inhibitor buffer were then added to each tube (the final concentration of $^{125}$I-rIL-2 was 0.5 nM). After 60 min. at 37° C., the tubes were centrifuged (10,000 ×g, 2 min.) to separate free from cell-associated $^{125}$I-rIL2. The tubes were cut and the cell associated and free radioactivity were determined by solid scintillation counting. Non-specific binding, determined in the presence of a 300 fold molar excess of unlabeled ligand, was <3% of total $^{125}$I-rIL2.

The solution K$_d$ (K$_{ds}$) for IL-2R beta cc was calculated from competitive binding data as previously reported (Johnson et al., 1994) assuming that binding had reached equilibrium with negligible reduction in the free IL-2 concentration and that only a single cell-associated receptor population makes a significant binding contribution. The equilibrium constant for IL-2 at the cell surface was 1.0×10$^9$ M-1 (Teshigawara et al., 1987).

Design of the Recognition Sequence—Our goal for this prototype fusion protein was to produce a stable noncovalent homodimer complex of the IL-2R beta-subunit ectodomain by substituting amino acid sequences (heptad repeats) that would generate stable coiled-coil association. Therefore, we designed a recognition sequence that included seven heptad repeats [FIG. 1 depicts helical wheel representations of the amino acid sequence (single letter code) of the coiled-coil heptad repeat design employed to direct the desired homodimer association. A single heptad is depicted with positions a b c d e f g (LEALEKK) (SEQ ID NO: 3) viewed along the helical axis from the top.] designed to favor self-association based upon a variety of reports that have examined the stability of peptides containing repeated coiled-coil heptads (Engel et al., 1991; Hodges et al., 1981; Hodges et al., 1990; Zhou et al., 1992). It should be noted that after this study was initiated, the use of native-like transcription factor leucine zipper sequences to assist the formation of Fv and bispecific antibody complexes was reported (Pack et al., 1992; Kostelny et al., 1992) lending support to this approach. Although several variations of the heptad repeat have been reported to generate this type of stability, we chose the LEALEKK (SEQ ID NO: 3) arrangement, a variation of the repeat examined by Hodges (Hodges et al., 1981; Zhou et al., 1992) and one chosen by Degrado for the study of helix forming tendencies of amino acids (O'Niel and Degrado, 1990). This heptad includes the following structural features: 1) it employs leucine residues at the hydrophobic interface of the two helices (a and d positions in the heptad) earlier reports suggested that leucines are preferable at these positions in coiled-coils to optimize knob-hole type packing (Hodges et al., 1990; O'Niel and Degrado, 1990), although the a position is more important in this respect (Zhou et al., 1992); 2) All of the residues have a high helical; propensity; and 3) the electrostatic charges are balanced and arranged such that interhelical salt bridges can form to stabilize helical association. A peptide composed of only four heptad repeats based on this sequence was shown to form greater than 90% coiled-coil stabilized helical structure at concentrations less than 2 µM at pH 7.5 even in the presence of 5M urea (O'Niel and Degrado, 1990). We incorporated 7 heptad repeats since we were uncertain what influence receptor ectodomains might have on the tendency of the ends of the coiled-coil segment to fray and destabilize the interaction. In addition, our goal was to achieve stable complexes at monomer concentrations below 1 µM.

At the time this study was initiated, the formation of dimeric complexes employing the recognition sequence chosen was supported by both experimental results and theoretical considerations. Recently, however, others who have employed similar heptad designs in efforts to prepare coiled-coil peptide dimers have observed trimer formation (Lovejoy et al., 1993). Careful examination of the roles of hydrophobes at the a and d positions of the heptad have now revealed that the presence or absence of B-branched residues at these positions determines the extent of oligomerization of the complex (Harbury et al., 1993; Zhu et al., 1993). When Leu residues are employed at both a and d positions in model peptides, the predominant oligomerization state is that of a trimer. Our study confirms this observation (see below). It is likely that in some of the earlier studies that formed the basis for our initial designs, the distinction between a dimeric and trimeric complex could not be made. Alternatively, the differences in residues chosen for the other heptad positions in these studies may have prevented trimer formation.

Construction of the Fusion Protein—Our goal of fusing coiled-coil sequences onto IL-2 receptor ectodomains required that we add 49 amino acid residues (7 heptad repeats) to the C-terminus of the extracellular receptor segment in place of the wild type transmembrane sequence. We generated the DNA sequence encoding the seven heptads in the pUC 19 bacterial vector. Two large double stranded synthetic oligonucleotide cassettes were prepared, each encoding approximately one half of the required heptad sequence. In addition, 5' and 3' restriction sites were added allowing both the directional insertion of the p75 ectodomain gene and cloning of the completed construction into an expression vector. The codon usage of the first cassette was chosen so as to incorporate these sites as well as a unique site in the middle of the sequence that would allow insertion of the second cassette.

Although straightforward in concept, the preparation of these modified receptor genes proved somewhat difficult in practice. First, the long synthetic oligonucleotides employed to prepare the cassettes had to be highly purified (HPLC-ion exchange chromatography). The presence of truncated segments even in reverse phase HPLC purified oligonucleotides prevented the proper annealing of two full length strands required to produce a cassette with the correct restriction site sequence overhangs. In addition, codon usage had to be adjusted so as to make the DNA sequence of each heptad slightly different from the others within the same strand to insure that improper annealing (i.e. out of register) was minimized. Using these precautions we were able to form the required cassette. Nevertheless, we still encountered an unusually high degree of recombination and cloning errors due to the similarities of the sequences encoding each heptad.

The p75 ectodomain cDNA segment was obtained from the full length receptor cDNA via PCR employing primers encoding the required restriction sites. This fragment was inserted into the pUC 19 vector harboring the coiled-coil gene and the entire fusion protein cDNA was verified by sequencing.

Protein Expression and Purification—In order to generate sufficient quantities of fusion protein for structural and biological characterization, we chose baculovirus mediated insect cell expression (Miller, 1988). This procedure had been employed for the expression of a variety of soluble receptor domains (Ota et al., 1991; Vissavajjhala and Ross, 1990) and we have successfully expressed the p75 ectodomain (IL-2Rb$_x$) itself using this methodology (Sana et al., 1994). Therefore, we subcloned the coiled-coil/receptor ectodomain construct prepared in pUC 19 between the BamH I and Nhe I sites in the baculovirus vector, pBlueBac II (Invitrogen). Following co-transfection of Sf9 cells with recombinant vector and wild-type AcNPV DNA, clones producing recombinant virus free of wild type contamination were identified and high titer virus was prepared. The kinetics of expression of the fusion protein were established by examination of Coomassie stained SDS-PAGE gels of crude cell culture supernatant (not shown). A band at approximately 37 kDa representing the putative fusion protein achieved maximum density at about 72 hours post infection. Subsequent infection of Trichoplusia (High-Five™, Invitrogen) cells established that levels of protein expression were approximately 10 fold greater than in Sf9 cells, therefore High-Five™ cells were employed for large scale protein preparation.

One-step affinity purification of IL-2R beta fusion protein complex was achieved using an IL-2 affinity column (Sana et al., 1994). Following elution from the column, the purity of the protein was demonstrated by a single band corresponding to IL-2R beta on SDS/PAGE and by a single peak on reverse phase HPLC chromatography [Reverse phase HPLC analysis of immunoaffinity purified IL-2R beta using a Dynamax 300A C18 (4.6×250 mm) column (Rainin). Buffers: A, 0.1% TFA in water; B, 0.1% TFA in acetonitrile; gradient, 25–75% solvent B over 45 min at a flow rate of 1 ml/min; absorbance was monitored at 215 nm.]. Amino terminal sequence analysis confirmed that the first 10 amino acids matched those of the published p75 sequence (Hatakeyama et al., 1989). Yields of up to 3 mg IL-2R beta per liter of supernatant were achieved.

Biophysical Properties of the IL-2R beta Complex—Comparison of the far UV circular dichroism spectrum of purified IL-2R beta complex with the spectrum of the p75 ectodomain alone clearly indicates the addition of a substantial amount of alpha-helical structure. [Far UV circular dichroism of purified (A) IL-2R beta ectodomain and (B) IL-2R beta fusion protein. Samples were prepared in 20 mM phosphate buffer, pH 7.0 containing 100 mM NaCl. The results are an average of 35–50 scans with buffer baseline subtracted. While IL-2R beta itself is not predicted to contain helix, minima at 208 and 222 nm in the spectrum of the IL-2R beta protein complex indicates the addition of significant helical structure (Wu and Ciardelli, 1994; © 1994 ESCOM Science Publishers B.V.).]. Deconvolution (Perczel et al., 1991) of the IL-2RBx spectrum had previously revealed less than 2% α-helix (~30–35% beta , 65–70% turns and unordered structure, Sana et al., 1994). This result was in accord with the expected secondary structure content of hematopoietic receptors exemplified by the HGHR (De Vos et al., 1992). When the spectrum of the IL-2R beta complex was analyzed, all additional~13% alpha-helix was predicted. This is consistent with greater than 75% of the seven heptad repeats existing in a helical conformation and likely indicates almost complete coiled-coil formation.

We then examined the behavior of the purified complex on gel filtration employing a calibrated HPLC size exclusion column. [Comparison of the IL-2RB ectodomain (A) and IL-2R beta complex (B) on size exclusion chromatography. The chromatogram was based on a summed overlay of single injections. Column: 7.5 mm×30 cm TSK-Gel G3000SWXL; buffer, 20 mM NaPO4, pH 7.0 containing 100 mM KCl, flow rate, 0.5 ml/min, absorbance monitored at 215 nm. Calibration was carried out using Sigma GF-200 gel filtration protein standards. The apparent MW of peak A (the free IL-2RB ectodomain) was determined to be 31 kDa and peak B (the IL-2RB complex) was determined to be 200 kDa.]. Comparison of the elution volumes of free IL-2R beta (B) with the free IL-2R beta (A) demonstrates that the complex elutes with a substantially larger size than the individual receptor ectodomain. According to the column calibration, however, the apparent molecular weight of the complex is 200 kDa, significantly larger than the MW of the expected homodimer complex (~70 kDa). Determination of the molecular weight of this complex using size exclusion chromatography is unreliable since IL-2R beta would not be expected to behave as a globular protein. If fully formed, the coiled-coil segment would create a rod like stalk that would extend approximately 75 Å (Philips, 1992). Upon gel filtration then, this complex should possess an anomalous retention volume as do molecules of similar structure such as kinesin heavy chain (Bloom et al., 1988).

In order to determine the true molecular weight and stoichiometry of the complex, we carried out equilibrium sedimentation. Four separate analyses on independently prepared samples showed that each sample could be fit adequately by a model consisting of a single thermodynamically ideal component. There was no evidence for a mass action association or nonideailty. However, there did appear to be a small amount of aggregated material whose contribution to these analyses was minimized by using data acquired at higher speeds. This was evidenced by the somewhat higher molecular weight for one of the samples and in the higher rpms than usually observed. For three of the four samples, the molecular weight was consistent with a trimeric complex (expected MW 110–115 kDa). In one experiment (Sample 2), the measured molecular weight was more consistent with a dimer. Although it is possible for the complex to exist in both dimeric and trimeric forms, it is unlikely since all of the samples were prepared in a similar fashion. It is more likely that the lower value obtained for the single sample was a result of degradation or the presence of lower molecular weight material. Significantly, no monomer was observed at any of the concentrations examined, confirming that the complex was extremely stable. Attempts to estimate the stability of the complex employing denaturants and CD analysis indicated that the globular ectodomain segment unfolded concomitantly with the coiled-coil domain.

Sedimentation velocity analyses on two samples (80 µg/ml and 50 µg/ml) were consistent with the sedimentation equilibrium studies. The major component (>95%) migrated at s20,w of 4.7±0.1, with a small amount (<5%) of 7.1±0.2 species detectable. Assuming that the complex behaves as a hydrated (0.4 $H_2O$/g protein) prolate ellipsoid, the axial ratio of the 4.7 species is between 11 and 12. The 4.7 s boundary has no trailing edge, consistent with there being no dissociation of the trimer.

Ligand binding Characterization—To quantitate the ligand binding ability of the complex, we performed radio-receptor competition assays on a cell line (YT-2C2) expressing only the intermediate affinity (B2) IL-2 receptor (Teshigawara et al., 1987). As depicted in FIG. 6, the IL-2 control displays the expected competition curve corresponding to a $K_d$ of approximately $3 \times 10^{-9}$M. When the competitive displacement curve of purified IL-2R beta was plotted with respect to p75 monomer content (determined by UV absorption), an $IC_{50}$ of $4.7 \times 10^{-7}$M was obtained corresponding to a Kds=$3.0 \times 10^{-7}$M. This curve was similar to the displacement curve obtained when IL-2RBx was used as the competitor. These results indicate that the IL-2R beta cc complex binds IL-2 in solution with an affinity comparable to the free p75 ectodomain based on its monomer content (i.e. each p75 ectodomain in the complex binds IL-2 with in affinity similar to the free ectodomain). This suggests that the process of complexation does not interfere sterically or allosterically with receptor ectodomain: ligand recognition.

The functional IL-2R is composed of at least three cell-surface subunits, each capable of interacting with ligand independently. On the cell surface, however, the subunits function cooperatively to form binding sites of much greater affinity than the individual subunits themselves. Mechanistically, IL-2R belongs to the class of hematopoietic receptors in which hetero-oligomeric subunit association is utilized to initiate signal transmission. Both alpha/beta- and beta/gamma- complexes form physiological binding sites (Landgraf et al., 1992; Caligiuri et al., 1990) while all three subunits are required to generate the high affinity receptor on activated T-cells.

The goal of this study was to evaluate the potential of coiled-coil molecular recognition to mediate stable solution assembly of receptor ectodomain subunits. We have chosen coiled-coil mediated assembly to form these complexes for several reasons. The nature of the hydrophobic heptad had been extensively studied and this recognition element was clearly capable of mediating stable homo-oligomeric and hetero-oligomeric solution complexes. The register of the double helical structure would also serve to hold the receptor ectodomains in proper orientation, a function provided by the hydrophobic membrane on the cell surface. Finally, the nature of the coiled-coil interaction itself could serve as a very close mimic of the interaction of the transmembrane segments of the receptor subunits. It is now well established that interhelical docking within the membrane is characteristic of many cell surface protein assemblies and in many cases, may be required for signaling (Bormann and Engelman, 1992; Lemmon et al., 1992; Sternberg and Gullick, 1990). The transmembrane segments of both beta- and gamma- IL-2R subunits possess sequence motifs diagnostic of intramembrane interaction (Sternberg and Gullick, 1990) suggesting that a coiled-coil like interaction may actually occur within the membrane upon IL-2 binding.

As an initial target, urge constructed a fusion protein designed to form a homodimeric complex of the IL-2R beta subunit. We began this study prior to the discovery of the IL-2Rgamma-subunit. Therefore, the significance of an IL-2R beta homodimer was of interest in light of the functional importance of HGHR and EPOR homodimers. In addition, our own studies of the behavior of the individual subunit ectodomains indicated that the p75 ectodomain was the only one of the three that exhibited no tendency to self associate at high concentrations (Sana et al., 1994) a phenomena that could confound interpretation of the complex formation.

Although the seven heptad repeats fused to the p75 ectodomain mediated the formation of a very stable complex (dissociation to monomer was undetectable at submicromolar concentrations as observed on HPLC gel filtration) and the anticipated structural features of the coiled-coil were observable in the CD spectrum, the size of the assembly was apparently greater than a dimer on gel filtration analysis. Analytical ultracentrifugation demonstrated that the complex was a trimeric assembly and possessed the elongated shape (hydrated dimensions approximately 36.6 nm×3.3 nm) expected for a protein composed of a globular head and a coiled-coil stalk. The trimeric nature of the complex is not surprising in light of the most recent studies of designed coiled-coil peptides.

Even as a trimer, the IL-2R beta complex was capable of binding IL-2 in a manner similar to the monomeric ectodomain on a subunit basis. This indicates that the nature of the coiled-coil complex did not interfere with ectodomain—ligand recognition, an observation that may prove significant in future studies of the formation of hetero-oligomeric subunit complexes where cooperativity in ligand binding is desired.

The ultimate goal of this study is to prepare stable heteromeric complexes of the IL-2R subunits for which solution binding mimics cell surface ligand interactions. Heterodimers of the alpha/beta- and beta/gamma-subunits were the intended targets of heteromeric complexation using the same Leu hydrophobe pair combined with segregation of the electrostatic residues to different coiled-coil helices in a fashion that should favor hetero- rather than homo-oligomeric association (Graddis et al., 1993). These designs should, however, also form trimers. In fact, preliminary results on the attempts to form alpha/beta- hetero-complexes based on these designs suggest that trimeric hetero-complexes do result that bind IL-2 with affinities higher than either of the individual component subunits.

The most recent results of peptide studies indicate that by the appropriate choice of residues occupying the a and d positions of the heptad, it is possible to design heptad sequences that associate in the parallel and heteromeric fashion required for the solution assembly of two different receptor ectodomains (Zhu et al., 1992; O'Shea et al., 1993; Harbury et al., 1993). For example, simple replacement of Leu by Ile in the a position of our designs should favor dimeric association.

With respect to the cell surface IL-2R, the high affinity site may be a heterotrimer of all three subunits. Our results suggest that the formation of a stable trimer complex is possible (although it was not possible to establish that all three subunits assembled in a parallel fashion). Considerably more challenging than heterodimeric assembly, the formation of an IL-2R heterotrimer in solution may be achievable as more is revealed on the nature of multimeric coiled-coil design (Cohen and Parry, 1994). Most hematopoietic receptors seem to function as heterodimers, however, (Cosman, 1993) and we believe that the current state of coiled-coil design is sufficient to prepare soluble versions of these cell surface complexes. In light of the significance of both homo- and heteromeric receptor aggregation in cytokine function, coiled-coil recognition may prove to be an efficient method for the stable solution assembly of receptor ectodomains in a manner that simulates their cell surface cooperativity. These complexes could facilitate ligand co-crystallization studies, serve as selection media for ligand affinity maturation studies, and provide high affinity binding reagents for diagnostic and therapeutic applications.

Example 2

This example refers to studies performed in various citations listed below. Each reference is hereby incorporated by reference in its entirety.

Although the high affinity IL-2R employs three subunits, hetero-oligomeric complexes involving only two of the IL-2R subunits play physiologically important roles. We have previously determined that the (alpha/beta) "pseudo high affinity" receptor exists, preformed, on the surface of activated T-cells and serves to capture ligand (Langraf et al., 1992). This observation was in accord with theoretical analyses of ligand binding data (Goldstein et al., 1992). Furthermore, the beta/gamma subunit intermediate affinity site exists on the majority of NK cells in the absence of the alpha-subunit (Caliguri et al., 1990). Therefore, the multimeric IL-2R may exist in several physiologically functional forms.

The ligand recognition properties of the individual subunit ectodomains have been studied. The soluble alpha-ectodomain binds IL-2 with an affinity similar to the cell surface low affinity site (Robb et al., 1987). We have demonstrated that the beta ectodomain is also capable of binding IL-2 in solution (Sana et al., 1994-which is hereby incorporated by reference in its entirety). Although the gamma ectodomain binds IL-2 very weakly in solution, we have found that it can bind cooperatively with the beta ectodomain to form a stable beta/gamma-ectodomain:IL-2 complex (Johnson et al., 1994-which is hereby incorporated by reference in its entirety).

We have prepared and characterized an IL-2R beta ectodomain/coiled-coil fusion protein (see example 1) and demonstrated the stable formation of a homotrimeric ectodomain complex capable of binding ligand. in this example, we describe the first solution assembly of a hetero-oligomeric cytokine receptor complex. This trimeric hetero-complex binds IL-2 with an affinity much greater than either the individual component subunit ectodomains or their homomeric coiled-coil complexes and in a manner that indicates subunit cooperativity. In addition, this complex binds IL-2 with an affinity similar to the comparable "pseudo high-affinity" cell surface IL-2 receptor. The designs of the coiled-coil heptads were based on previous studies of the stability of peptide coiled-coils (Zhou et al., 1992 and O'Niel et al., 1990). Seven repeats of the sequence LEALKEK (SEQ ID NO: 1) were employed as the recognition element for the alpha-subunit ectodomain (IL-2R alpha cc), while seven repeats of LKALEKE (SEQ ID NO: 4) were chosen for the beta subunit ectodomain (IL-2R beta cc). These sequences employ Leu residues at both the a and d positions of the heptad with like-charged residues at the e and g positions of each helix to favor heteromeric over homomeric association based on electrostatic interactions (Graddis et al., 1993). In one version of the alpha-subunit coiled-coil construct (IL-2R alpha cc tag), a DNA sequence encoding the peptide epitope tag, EYMPME (SEQ ID NO: 5), (Johnson et al., 1994) was added to the C-terminus to facilitate affinity purification of the protein. Earlier studies employing synthetic peptides indicated that these designs might mediate the formation of heterodimers. Recent reports, however, confirm that designs employing Leu residues at both the a and d positions favor the formation of trimers (FIG. 1) (Lovejoy et al.,1993; Zhu et al., 1993; Harbury et al., 1993).

Generally, for preparation of the fusion proteins, the cDNA segments encoding the seven coiled-coil heptad repeats were constructed in pUC vectors from two large synthetic oligonucleotide cassettes as previously described for the homomeric complex (Wu et al., 1994). The cDNAs encoding the alpha- and beta- subunit ectodomains were inserted 5' to DNA sequences representing these repeats. Baculovirus mediated insect cell expression was employed for the production of the recombinant fusion proteins by simultaneous co-infection with both IL-2R alpha cc and IL-2R beta cc recombinant virus. Insect cell expression had proven successful both for the expression of the individual IL-2R ectodomains (Sana et al., 1994; Johnson et al., 1994) as well as for the IL-2R beta homo-oligomeric complex (Wu et al., 1994).

Specifically, the fusion proteins were constructed as follows: The cDNA for the beta-subunit fusion protein possessing the LKALEKE (SEQ ID NO: 4) heptad repeat was constructed in pUC-19. The first double stranded oligonucleotide cassette encoding approximately one half of the seven heptad repeat segment, a 5' Nhe I site, and two Dsa I sites for directional cloning of the beta-subunit ectodomain was inserted at the BamH I site in pUC-19. After verification of sequence and orientation, the second double stranded cassette completing the coiled-coil cDNA was inserted between A II and Bst B1 sites of cassette 1. The cDNA encoding the beta-subunit ectodomain obtained as described was directionally inserted between the two Dsa I sites. The resulting IL2R beta cc sequence was removed from pUC 19 (Nhe I and BamH I) and subcloned into the pBlueBac II baculovirus expression vector (Invitrogen) and verified by sequencing. Similarly, the cDNA encoding the alpha-subunit fused to the LEALKEK (SEQ ID NO: 1) coiled-coil repeat was constructed in pUC-8. The first cassette encoding a 5' Xba I site in addition to the coiled-coil cDNA was inserted at the BamH I site in pUC8. The second cassette with the remaining coiled-coil cDNA was inserted between Xho I and Afl II sites in the first cassette. The cDNA encoding the alpha subunit ectodomain was directionally cloned between the BamH I and Xba I sites. The complete fusion protein cDNA was the removed from pUC-8 (BamH I and Bgl II) and subcloned into the BamH I site of pBlueBac II baculovirus expression vector (Invitrogen). The sequence and orientation were verified by sequencing.

High titer recombinant virus was then prepared. Trichoplusia ni (High-Five) insect cells were simultaneously co-infected with IL-2R beta cc and IL2R alpha cc recombinant virus and the cell free culture supernatants were collected 72 hours post infection.

Initial co-infections were carried out employing IL-2R alpha cc tag virus, therefore, preliminary purification was carried out by passing the harvested cell supernatant over an anti-epitope tag immunoaffinity column. Preliminary experiments comparing the ability of the bound fraction to inhibit IL-2 activity in competitive bioassays (Johnson et al., 1994), indicated that the complex isolated from the mixed subunit co-infection was 50 to 100 fold more potent than a homomeric complex of IL-2R alpha cc tag. Although not designed to be quantitative, these experiments suggested the presence of a mixed subunit complex with greatly enhanced binding affinity.

Figure 2:
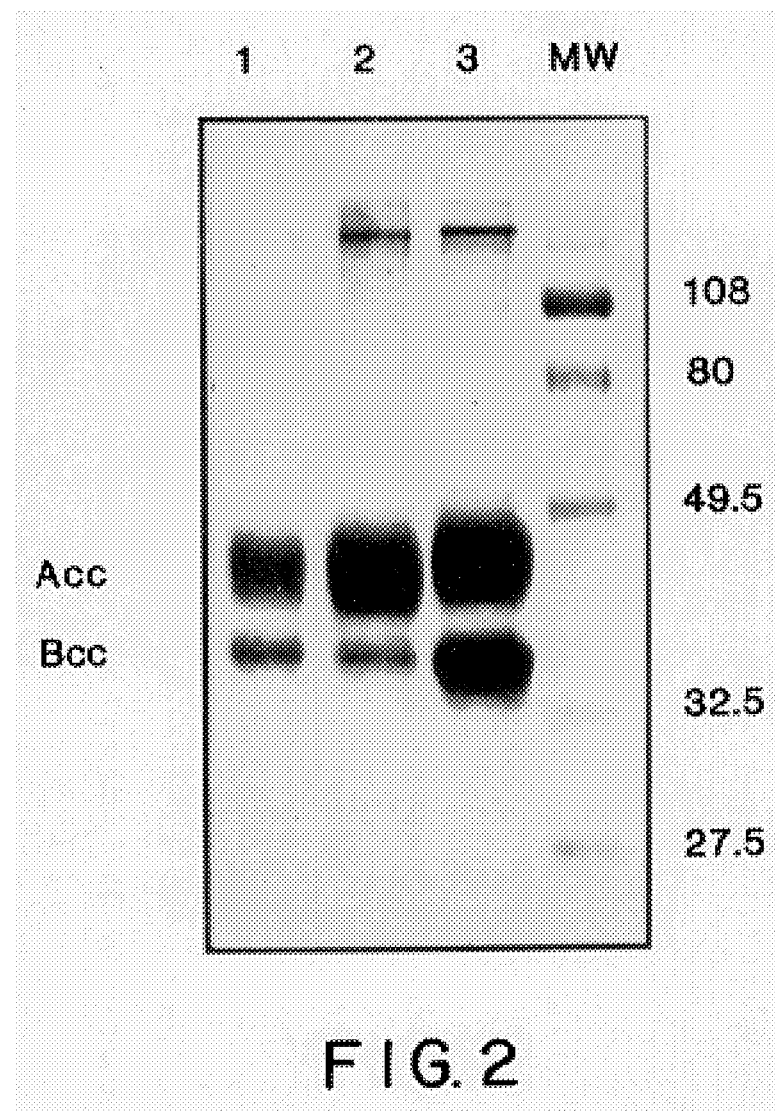
FIG. 2. SDS-PAGE analysis of immunoaffinity purification of the alpha/beta cc complex (Coomassie blue stained). Lane 1, the fraction of co-infection cell supernatant bound to the alpha ectodomain specific tag epitope affinity column; Lane 2, the flow through fraction obtained when the tag epitope bound sample (lane 1) was applied to a beta ectodomain specific immunoaffinity column; Lane 3, the fraction bound to the beta ectodomain specific inununoaffinity column, the alpha/beta cc (Acc and Bcc) complex. Acc and Bcc mark the positions of the alpha and beta subunit coiled-coil fusion proteins, respectively.

In order to isolate the stably-associated complex of both receptor ectodomains, the bound fraction obtained from the epitope immunoaffinity column (alpha-subunit specific) was applied to an immunoaffinity column specific for the beta-subunit ectodomain (TIC antibody, (Sana et al., 1994). SDS-PAGE analysis of the fraction bound to this second column confirmed enrichment of beta-subunit fusion protein when compared to the starting mixture or column flow through (FIG. 2). Competitive bioassays revealed that the fraction that bound to both columns was 2 fold more potent than the initial tag-column bound fraction and 3 fold more potent than the TIC flow through fraction (Competitive neutralization of bioactivity was determined as previously described in Johnson et al., 1994 on Kit 225 cells. The $IC_{50}$ for the TIC bound fraction was 0.2 μg/ml while that for the column flow through fraction was 0.6 μg/ml. The $IC_{50}$ for the starting mixture was 0.4 μg/ml.). N-terminal sequence analysis of the TIC column bound hetero-complex revealed a 2:1 stoichiometry of alpha-subunit to beta-subunit ectodomain protein (Automated N-terminal Edman sequencing of the complex present in the TIC column bound fraction matched the published amino acid sequence of both alpha- and beta- receptor subunit. 7 cycles: alpha-subunit; E(62 pM), L(51 pM), X(0.7), D(41 pM), X(NA),D(0.4 pM), P(43 pM): beta-subunit; A(39 pM), V(27 pM), X(0.4 pM), G(20 pM), T(15 pM), X (NA), Q (20 pM). The alpha/beta ratio of cycles 1,2,4 and 7=1.6,1.9, 2.1, 2.2, resp., Cycles 3, 5 and 6 occur at unstable or glycosylated positions in one or both subunits.).

Figure 3:
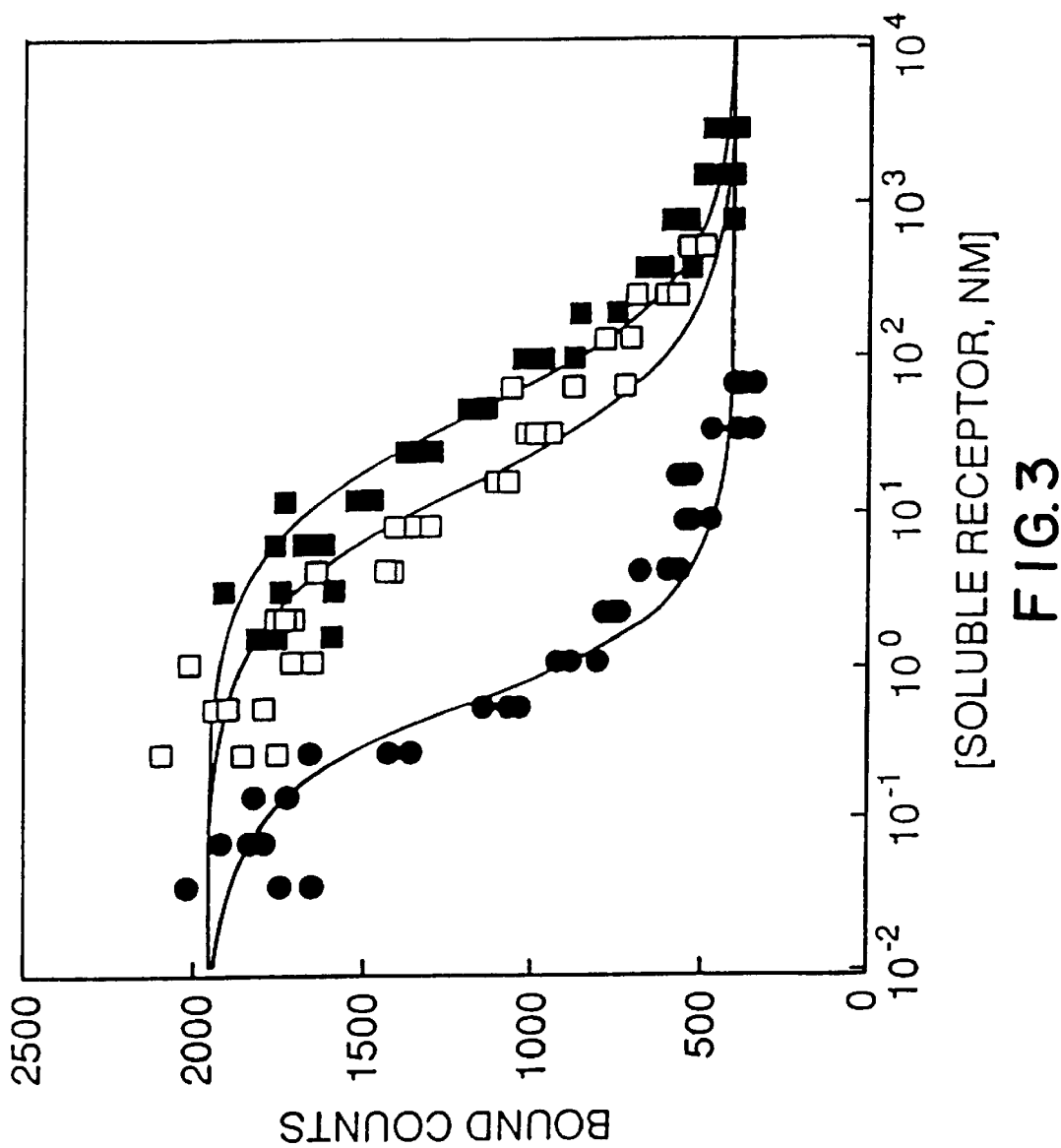
FIG. 3. Competitive displacement of $^{125}$I-IL-2 on MT-1 cells. Total bound radioactivity is plotted versus concentration of soluble receptor for the alpha/beta cc complex (circles), the alpha cc complex (open squares) and an equimolar mixture of alpha and beta ectodomains (solid squares). Maximum cpm bound in the absence of competitor (2085+47 cpm) was obtained from the average of six determinations. The assay was performed at 37° C. under conditions where the depletion of free $^{125}$I-IL-2 is negligible. Thus, the fraction of maximum bound $^{125}$I-IL-2, b=c $(1+K^*C^*_T)/(1^*cK^*C^*_T)$, where $C^*_T$ is the total concentration of $^{125}$I-IL-2 (500 pM), C*s the concentration of $^{125}$I-IL-2 in the presence of soluble receptor, $c=C^*/C^*_T$, and K* is the equilibrium constant for $^{125}$I-IL-2 binding to the cell surface alpha-subunit on MT-1 cells. In the nonlinear least-squares fits to the data (solid curves) we took the concentration of $^{125}$I-IL-2 bound to soluble receptor to be $K_{eq} C^* R_T/(1+K_{eq} C^*)$, where $R_T$ is the total concentration of soluble receptor (x axis) and $K_{eq}$ is an equilibrium binding constant for the binding of $^{125}$I-IL-2 to the soluble receptor (see ref. 29 for a discussion of $K_{eq}$ for each type of complex). Since the total concentration of $^{125}$I-IL-2 remains unchanged, $C_{*T}=C^*+K_{eq}C^*R_T/(1+K_{eq}C^*)$, which is a quadratic equation that can be solved for c and c can then be substituted into the expression for b. The following equation for total radioactivity bound, cpm, was used to fit the data: cpm=ns+(cpm (O)−ns)b, where ns is the amount of nonspecifically bound $^{125}$I-IL-2(410 cpm, visible as noncompetable cpm in figure). In control experiments where unlabeled IL-2 was used to compete $^{125}$I-IL-2, we determined that the $K_{eq}$ for unlabeled binding to the alpha-subunit on MT-1 cells was $2.0\times10^7$ M$^{-1}$ (three separate experiments). When fitting the soluble receptor data we took K* equal to this value.

Since this hetero-oligomeric complex was the most potent ectodomain related inhibitor tested in the competitive bioassay, we carried out a quantitative ligand binding study to determine the solution affinity. In order to exclude any potential interference by the tag epitope sequence, we created another alpha ectodomain/coiled-coil fusion protein lacking this sequence and isolated the hetero-oligomeric complex from co-infection supernatants by sequential affinity columns employing monoclonal antibodies (mAbs) specific for each ectodomain (alpha; TAC (Leonard et al., 1992): beta; TIC (Sana et al., 1994). Then, employing a competitive radio-ligand binding assay on the MT-1 cell line, a line in which IL-2 binds to the single cell surface alpha-subunit at the concentrations used (Wang and Smith, 1987), we compared the ligand affinity of the alpha/beta cc hetero-complex to a similar complex composed of the a-subunit alone (alpha cc) and to a mixture of individual, uncomplexed alpha- and beta- ectodomains (FIG. 3).

The results of the competitive binding assay clearly demonstrate that the alpha/beta cc complex is a much more efficient competitor than the other two preparations. Since the complex is a multimer of subunits each of which is potentially capable of binding ligand independently, it is important to distinguish cooperative binding from the potential effects of avidity due to simple multivalency. To quantify our results and demonstrate cooperativity, we calculated an effective dissociation constant for the complex ($K_d$) as described in FIG. 3 from the equilibrium binding constants ($K_d=1/K_{eq}$) listed in Table 1 (The equilibrium binding constants were determined from nonlinear least-squares fitting of the competitive displacement data in FIG. 4. It was assumed that the amount of $^{125}$I-IL-2 specifically bound to soluble receptor, $B^*=K_{eq}C^*R$, where $C^*$ is the concentration of free $^{125}$I-IL-2 and R is the concentration of free soluble receptor. When the soluble receptor is an equimolar mixture of alpha and beta ectodomains without aggregation, $K_{eq}=(K_{alpha}+K_{beta})$, where $K_{alpha}$ and $+K_{beta}$ are the equilibrium constants for the binding of $^{125}$I-IL-2 to the individual ectodomains. Since $K_{alpha}>K_{beta}$, $K_{alpha}$ is approximately $K_{eq}=2.4\times10^7$ M$^{-1}$. When the soluble receptor is alpha cc and the three sites act independently, $K_{eq}=3$ $K_{alpha}$, and $K_{alpha}=2.3\times10_7$ M$^{-1}$. These values of $K_{alpha}$ are in good agreement with the values for the equilibrium constant, $2.0\times10^7$ M$^{-1}$, that we determined for the binding of unlabeled IL-2 to the low affinity receptor on MT-1 cells. If the three chains in the alpha/beta cc complex acted independently, then we would expect $K_{eq}(2 K_{alpha}+K_{beta})/3$ is approximately 2 $K_{alpha}/3=1.3\times10^7$ M$^{-1}$. Since the experimentally determined value of $K_{eq}=3.1\times10^9$ M$^{-1}$, the binding is apparently highly cooperative. The estimates of $K_{eq}$ were determined by nonlinear least-squares data fitting as discussed in FIG. 4. Estimates of the standard errors of $K_{eq}$ were obtained using a bootstrap method (Efron et al., 1986) where 150 simulations were performed for each estimate. If the ectodomains of the complex act independently, then $K_d=3/(2 K_{alpha}+K_{beta})$, where $K_{alpha}$ and $K_{beta}$ are the equilibrium constants for the binding of labeled IL-2 to the alpha and beta ectodomains respectively. If the binding is positively cooperative, then the $K_d$ will be smaller than this value while negative cooperativity will yield a greater value. We estimate (Table 1) that for noncooperative binding, $K_d$ is substantially equivalent to 76 nM. Nonlinear least-square analyses of the competitive binding data (FIG. 3) yield Kd=0.32 nM for the heteromeric complex, $K_d=15$ nM for the alpha cc complex and $K_d=42$ nM for the mixture of individual components (previously, we determined that for the beta cc trimeric complex, $K_d=300$ nM per beta -ectodomain or $K_d$ is substantially equivalent to 100 nM for the complex (Wu et al., 1994). Therefore, the results indicate that binding for the alpha/beta cc complex is highly cooperative and indicate that the alpha/beta cc complex is an efficient competitor at concentrations below 1 nM, where one to one: ligand to complex stoichiometry occurs and occupancy of the third alpha-ectodomain is insignificant. In addition, the data suggests that binding of the homo-oligmeric alpha cc complex is consistent with each alpha- ectodomain binding independently (as was previously observed for the beta cc complex), while for the mixture of alpha and beta ectodomains, there is no detectable subunit association in the absence of the recognition sequences. The efficiencies of these complexes to inhibit IL-2 bioactivity in a human HPBL bioassay (Landgraf et al., 1992) were also compared (FIG. 4). The $IC_{50}$ value obtained for the alpha/beta cc complex (approx. 0.9 nM) was slightly greater than its $K_d$ (0.32 nM), the $IC_{50}$ value obtained for the alpha cc trimer (approx. 100 nM) was significantly greater than its $K_d$, (15 nM). The beta cc homo-oligomeric complex did not compete in this assay at concentrations in excess of 1 micro molar. Similar results were obtained in the murine CTLL-2 bioassay (Gillis et al., 1978) where the $IC_{50}$ values were 2 nM and 500 nM for the alpha/beta cc and alpha cc complexes, respectively. The rapid dissociation rate from the alpha and beta-subunits (Wang and Smith, 197; Matsuoka et al., 1993) compared to the slower dissociation rate from the alpha/beta- "pseudo high affinity" site (Matsuoka et al., 1993) may account for tile reduced efficiency of competition for the homo-oligmeric complexes over the 24 hour bioassay. The 100 fold increase in potency for the hetero-oligomeric complex compared to the homo-oligomeric alpha cc complex provides further support for the cooperative nature of ligand binding.

In the previous example, the molecular weight of the trimer complex was determined by analytical ultracentrifugation (Wu et al., 1994). Therefore, we analyzed the hetero-complex by both equilibrium sedimentation and sedimentation velocity techniques (Analytical ultracentrifugation was performed on a Beckman XL-A analytical ultracentrifuge equipped with Rayleigh interference optics (Laue et al., 1994) using the methods previously described for the alpha/beta cc complex (Cosman, 1993)). The partial specific volume for the complexes was calculated assuming a protein molecular weight of 31,194 for the alpha-subunit (v0.73 ml/g) and 30,447 for the beta-subunit (v0.74 ml/g) and a carbohydrate molecular weight (v0.63 ml/g) of 12,200 g/mol and 8,400 g/mol for the alpha-subunit and beta-subunit, respectively (see Cosman, 1993). Sedimentation velocity was conducted at 50,000 rpm and the sedimentation coefficient distributions (g(s*)) were determined from the time derivative of the concentration profile as was described for the beta cc complex (Cosman, 1993). Equilibrium sedimentation studies were consistent with a trimeric complex with no significant evidence of monomer at any of the concentrations studied. Comparison with the IL-2R beta cc complex previously examined (Wu et al., 1994) indicates that the hetero-oligomeric complex is at least as stable as the IL-2R beta-homotrimer. Sedimentation velocity experiments were consistent with sedimentation equilibrium results. At concentrations below 0.25 mg/ml, the major component migrated at $S_{20,w}$ of 4.64.8. At 0.52 mg/ml, the major peak was at 4.3 s (FIG. 5). All curves provide some evidence for minor amounts of smaller and larger species, but there is no evidence for either mass action association or dissociation. The decrease in s with increasing concentration is expected for a non-interacting asymmetric molecule (Van Holde 1985). The hetero-complex migrates as an extremely asymmetric molecule with an axial ratio of about 15 (assuming a hydrated (0.4 $H_2O$/g protein) prolate ellipsoid). This shape is consistent with globular ectodomains fused to an extended (about 75 Å) coiled-coil stalk. Analytical ultracentrifugation analyses of the alpha cc complex indicated similar trimeric association.

In this study we have employed coiled-coil heptad repeats as recognition elements to mediate the solution assembly of receptor ectodomains that normally function cooperatively in cell surface ligand capture (Landgraf et al., 1992). We employed seven coiled-coil heptads in order to achieve complex stability at submicromolar monomer concentrations. The results of the competitive ligand binding assays confirm that the stability of the alpha/beta cc complex extends into the subnanomolar range since significant competition is observable at these concentrations. The effectiveness of the use of like-charged electrostatic residues at positions e and g of the heptad positions to favor heteromeric over homomeric association is uncertain. The alpha cc trimeric complex in which each monomer carried like charged residues at these positions was also stable. Although electrostatic interactions can direct hetero-oligomeric coiled-coil association (Graddis et al., 1993; O'Shea et al.,1993), the contribution of electrostatic interactions is less significant than hydrophobic interactions to the overall stability of coiled-coil complexes. High resolution studies of triple stranded coiled-coil peptides suggest that like-charged side chains have sufficient flexibility to avoid close approach (Lovejoy et al., 1990). Coiled-coil sequences from transcription factors have been employed previously to help mediate the formation of antibody complexes (e.g. see Kostelny et al., 1992). Unlike these studies, we have chosen idealized coiled-coil sequences due to their inherently greater stability. In addition, our goal was to assemble a cooperative system using non-covalent complexation. Cooperativity in ligand binding by the alpha- and beta- IL-2R subunits in the alpha/beta cc complex is evident from the 45 and 300 fold increases in affinity compared to the homo-oligomeric complexes of alpha and beta- subunits, respectively. How closely the alpha/beta cc complex mimics ligand binding by the cell surface alpha/beta-"pseudo high affinity" site is difficult to determine. Values varying between 100 pM and 600 pM are often reported for the affinity of alpha/beta-receptor when the individual subunits are transfected into non-lymnphoid cell lines (Matsuoka et al., 1993; Nakarai et al., 994; Minami et al., 1994). The reason for this variation may be due to cell type or the ratio of subunits expressed, nevertheless, the $K_d$ value for our alpha/beta cc complex is within the range of these reported values. Although the subunit stoichiometry of the soluble hetero-complex is not 1:1, neither is the ratio of alpha to beta IL-2 receptor subunits on the surface of most cells (Wang and Smith, 1987; Caliguri et al., 1990; Nakarai et al., 1994) and it is highly likely that soluble ligand binding resembles, at least in part, the functional form of the cell surface "pseudo high affinity" site.

Ligand induced receptor subunit cross linking to form both homo-oligmeric and hetero-oligomeric complexes is a hallmark of the hematopoietin receptor family (Cosman, 1993). The nature and stoichiometry of subunit association and ligand binding is often difficult to assess on the surface of cells. Refinements in the designs of coiled coil peptide complexes now make it possible to prepare stable assemblies containing two, three or four subunits (Zhu et al., 1993; Harbury et al., 1993) as well as to direct the formation of hetero-oligomeric complexes (Graddis et al., 1993; O'Shea et al., 1993). This is the first study to demonstrate the feasibility of employing coiled-coil designs as recognition units to mediate the solution assembly of hetero-oligomeric cytokine receptor complexes. This approach can easily be extended to other receptor complexes composed of two to four similar or different subunits to potentially provide reagents for detailed receptor subunit and ligand binding characterization, crystallographic analyses, selection of novel ligands from random libraries or in vivo therapeutic evaluation.

The previous examples have been used to show preferred features of the invention and should not be construed as limiting the invention in any way. The invention is to be construed in accordance with the following claims.

REFERENCES

Alber, T. (1992) Curr. Opin. Gen. Dev. 2, 205–210.

Arakawa, T. and Yphantis, D. A (1987) J. Biol. Chem. 262, 7484–7485.

Bazan, J. F. (1989) Biochem. Biophys. Res. Conmmun. 164, 788–796.

Bazan, J. F. (1990) Immun. Today 11, 350–354.

Bloom, G. S., Wagner, M. C. Pfister, K. K. and Brady, S. T. (1988) Biochemistry 27, 3409–3416.

Bormann, B. J. and Engelman, D. M. (1992) Annu. Rev. Biophys. Biomol. Struct. 21, 223–242.

Caligiuri, M., Zmuidzinas, A., Manley, T. J., Levine, H., Smith, K. A. and Ritz, J. (1990) J. Exp. Med. 171, 1509–1526.

Cohen, C. and Parry, D. A. D. (1990) Proteins 7, 1–15.

Cohen, C. and Parry, D. A. D. (1994) Science 263, 488–498.

Cosman, D. (1993) Cytokine 5, 95–106.

Cosman, D., Lyman, S. D., Idzerda, R. L., Beckmann, M. P., Park, L. S., Goodwin, R. G. and March, C. J. (1990) TIBS 15, 265–270.

Crick, F. H. C. (1953) Acta Crystallogr. 6, 689–697.

De Vos, A. M., Ultsch, M. and Kossiakoff, A. A. (1992) Science 255, 306–312.

Dukovich, M., Wano, Y., Bich Thuy, L. T., Katz, P., Cullen, B. R., Kehrl, J. H. and Greene, W. C. (1987) Nature. 327, 518–522.

Efron, B. and Tibshirani, R. Stat. Sci 1, 54–77 (1986).

Engel, M., Williams, R. W. and Erickson, B. W. (1991) Biochemistry 30, 3161–3169.

Gillis, S., M. M. Ferm, W. Ou and K. A. Smith J. Immunol. 121, 2077 (1978).

Giri, A. Ahdieh, J. Eisenman, EMBO J. 13, 2822 (1994).

Goldstein, B., Jones, D., Krevrekidis, I. G. and Perelson, A. S. (1992) Internat. Immunol. 4, 23–32.

Graddis, T. J., Myszka, D. G. and Chaiken, I. M. (1993) Biochemistry 32, 12664–12670.

Harbury, P. B., Zang, T., Kim, P. S., and Alber, T. (1993) Science 262, 1401–1408.

Hatakeyama, M., Tsudo, M., Minamoto, S., Kono, T., Doi, T., Miyata, T., Miyasaka, M. and Taniguchi, T. (1989), Science 244, 551–556.

Hodges, R. S. (1979) Polymer Preprints 20, 51–54.

Hodges, R. S., Saund, A. K., Chang, P. C. S., St. Pierre. S. A. and Reid, R. E. (1981) J. Biol. Chem. 256, 1214–1224.

Hodges, R. S., Sodek, J., Smillie, L. B. and Jurasek, L. (1972) Cold Spring Harbor Symp. Quant. Biol. 37, 299–310.

Hodges, R. S., Zhan, N. E., Kay, C. M. and Semchuk, P. D. (1990) Peptide Res. 3, 123–137.

Johnson, K., Choi, Y., Wu, Z., Ciardelli, T., Granzow, R., Whalen, C., Sana, T., Pardee, G., Smith, K. and Creasy, A. (1993) Eur. Cytokine Netw. 5, 23–34.

Johnson, M. L., Correia, J. J., Yphantis, D. A. and Halvorson, H. R. (1981) Biophys. J. 36, 575–588.

Johnson, W. D. (1990) Proteins: Struct. Funct. Gen. 7, 205–214.

Kondo, M., Takeshita, T., Ishii, N., Nakamura, M., Watanabe, S., Arai, K., and Sugamura, K. (1993) Science 262, 1874–1877.

Kostelny, S. A., Cole, M. S. and Tso, J. Y. (1992) J. Immunol. 148, 1547–1553.

Landgraf, B. E., Goldstein, B., Williams, D. P., Murphy, J. R., Sana, T. R., Smith, K. A. and Ciardelli, T. L. (1992) J. Biol. Chem. 267, 18511–18519.

Landschulz, W. H., Johnson, P. F. and McKnight, S. L. (1988) Science 240, 538–542.

Laue, T. M., Shah, B. D., Ridgeway, T. M. and Pelletier, S. M., Analytical Ultracentrifugation in Biochemistry and Polymer Science. S. Harding, A. Rowe, J. C. Horton, Eds., (Royal Society of Chemistry, London, 1992) pp. 90–125.

Laue, T. M. Analytical Ultracentrifugation in Biochemistry and Polymer Science. S. Harding, A. Rowe, J. C. Horton, Eds., (Royal Society of Chemistry, London, 1992) pp 63–89.

Laue, A. L. Anderson and P. D. Demaine Prog. in Coll. and Polymer Sci. 94, 74–81 (1994).

Lemmon, M. A., Flanagan, J. M., Hunt J. F., Adair, B. D., Bormann, B. J., Dempsey, C. E. and Engelmann, D. M. (1992) J. Biol. Chem. 267, 7683–7689.

Leonard, W. J. et al. Nature 300, 267 (1982.).

Lovejoy, B., Seunghyon, C., Cascio, D., McRorie, D. K., DeGrado, W. F. and Eisenberg, D. (1993) Science 259, 1288–1293.

Matsuoka, M., et al. Eur. J. Immunol. 23, 2472 (1993).

Miller, L. K. (1988) Ann. Rev. Microbiol. 42, 177–199.

Minami, Y., Kono, T., Miyazaki, T. and Taniguchi, T. (1993) Annu. Rev. Immunol. 11, 245–67.

Minami, Y., et al. J. Immunol. 152, 5680 (1994).

Nakarai, T., et al. J. Exp. Med. 180, 241 (1994).

Nakamura, Y. et al. Nature 369, 330 (1994).

Nikaido, T., Shimizu, A., and Ishida, N. (1984) Nature 311, 631–635.

Noguchi, M., Nakamura, Y., Russell, S. M., Ziegler, S. F., Tsang, M., Cao, X., and Leonard, W. J. (1993a) Science 262: 1877–1880.

Noguchi, M., Yi, H., Rosenblatt, H. M., Filipovich, A. H., Adelstein, S., Modi, W. S., O. W., M. and Leonard, W. J. (1993) Cell 73, 147–157.

O'Niel, K. T. and Degrado, W. F. (1990) Science 250, 646–651.

O'Shea, E., Lumb, K. J. and Kim, P. S. (1993) Curr. Biol. 3, 658–667.

Ota, Y., Asakura, A., Matsuura, Y., Kondo, H., Hitoshio, A., Iwane, A., Tanaka, T., Kikuchi, M. and Ikehara, M. (1991) Gene 106, 159–164.

Pack, P and PlYckthun, A. (1992) Biochemistry 31, 1579–1584.

Parry, D. A. D., Minasian, E. and Leach, E. J. (1988) J. Mol. Recog. 3, 107–110

Parry, D. A. D., Minasian, E. and Leach, S. J. (1991) J. Molec. Recog. 4, 63–77.

Perczel, A. Hollosi, M., Tusnady, G. and. Fasman, G. D. (1991) Protein Eng. 4, 669–679.

Philips, G. N. (1992) Proteins: Struct. Func. Gen. 14, 425–429.

Robb, R. J. and R. M. Kutney J. Immunol. 137,142 (1987).

Russel, S. M., Keegan, A. B. Harada, N. Nakamura, Y., Noguchi, M., Leland, P., Friedman, M., Miyajima, A., Puri, R. K., Paul, W. E. and Leonard, W. J. (1993)Science 262: 1880–1883.

Sabe, H., Kondo, S. K., Shimizu, A., Tagaya, Y. and Yodoi, J. (1984) Mol. Biol. Med. 2, 379–388.

Sana, T., Z. Wu, K. Smith and T. Ciardelli Biochemistry, 33, 5838–5845 (1994).

Sharon, M., Klausner, R. D., Cullen, B. R., Chizzonite, R. and Leonard, W. J. (1987) Science 234, 859–863.

Shire, S. (1992) Technical Information Bulletin DS 833 Beckman Instruments, Inc., Palo Alto Calif.

Smith, K.A. (1988) Science 240, 1169–1176.

Stafford, W. F. III (1992) Anal. Biochem. 203, 295–301.

Stahl, N. and Yancolopoulos, G. D. (1993) Cell 74, 587–590.

Sternberg, M. J. E. and Gullick, W. J. (1990) Prot. Eng. 3, 245–248.

Summers, M. D. and Smith, G. E. (1987) Texas Agricultural Experiment Station Bulletin No. 1555. College Station, Tex.

Takeshita, T., Asao, H., Ohtani, K., Ishii, N., Kumaki, S., Tanaka, N., Munakata, H., Nakamura, M. and Sugamura, K. (1992a) Science 257, 379–382.

Takeshita, T., Ohtani, K., Asao, H., Kumaki, S., Nakamura, M. and Sugarmura, K. (1992b) J. Immunol. 148, 2154–2158.

Talbot, J. A. and Hodges, R. S. (1982) Accts. Chem. Res. 15, 224–230.

Teshigawara, K., Wang, H.-M., Kato, K. and Smith, K. A. (1987) J. Exp. Med 165, 223–238.

Tsudo, M., Kozak, R. W., Goldman, C. K. and Waldmann, T. A. (1986) Proc. Natl. Acad. Sci. U.S.A. 83, 9694–9698.

Van Holde, K. E., Physical Biochemistry, (Prentice Hall, 2nd Ed.,1985) Vissavajjhala, P. and Ross, A. (1990) J. Biol.Chem. 265, 4746–4752.

Wang, H. M. and Smith, K. A. (1987) J. Exp. Med. 166, 1055–1069.

Wu, Z. and Ciardelli, T. L. Peptides: Chemistry, Structure and Biology (Proceedings of the 13th American Peptide Symposium) R. S. Hodges and J. A. Smith, Eds., (ESCOM, Leiden, 1994) pp 1038–1040.

Wu et al. Protein. Eng. (in press), (1994).

Yphantis, D. A (1960) Ann. NY Acad. Sci. 88, 586–601.

Zhou, N. E., Kay, C. M. and Hodges, R. S. (1992) Biochemistry 31, 5739–5746.

Zhou, N. E., Kay, C. M. and Hodges, R. S. (1992) J. Biol. Chem. 267, 2664–2670.

Zhou, N. E., Kay, C. M. and Hodges, R. S. Biochemistry (1993) 32, 3178–3187.

Zhu, B.-Y., Zhou, N. E., Kay, C. M. and Hodges, R. S. (1993) Prot. Sci. 2, 383–394.

Zhu, B.-Y., Zhou, N. E., Semchuck, P. D., Kay, C. M. and Hodges, R. S. (1992) Int. J. Prot. Pep. Res. 40, 171–192.

The scope of the invention is not to be limited by the illustrative embodiments set forth herein, but is to be determined in accordance with the appended claims.

TABLE 1

EQUILIBRIUM BINDING CONSTANTS

| Soluble IL-2 Receptor | $K_{eq}$ $(nM^{-1})$* |
|---|---|
| $\alpha\beta cc$ | $3.1 \pm 0.5$ |
| $\alpha cc$ | $0.068 \pm 0.007$ |
| $\alpha + \beta$ (mix) | $0.024 \pm 0.003$ |

*See reference (29)

TABLE 2

ANALYTICAL ULTRACENTRIFUGATION
$\alpha\beta cc$ IL-2R COMPLEX

| | Conc.* (mg/ml) | Rotor Speed†(rpm) | Mz‡ (kDa) | r.m.s.§ |
|---|---|---|---|---|
| Sedimentation Equilibrium | 0.52, 0.26, 0.13 | $20,25,30,35 \times 10^3$ | 111.9 (104.7–119.0) | 0.031 |
| | Conc.* (mg/ml) | Rotor Speed(rpm) | $S_{20.w_{fl}}$ | |
| Sedimentation Velocity | 0.52 | $50 \times 10^3$ | 43 | |
| | 0.25 | $50 \times 10^3$ | 4.7 | |
| | 0.08 | $50 \times 10^3$ | 4.6 | |

*Cell loading concentration used in combined analysis.
†Rotor speed used in combined analysis.
‡Apparent Z-averaged MW (32). Values in parentheses indicate the 95% confidence interval.
§r.m.s. of variance of fit to a model consisting of a single ideal thermodynamic component.
f1Determined from the time derivative of the concentration profile (32).

We claim:

1. A hetero-oligomeric high affinity binding complex comprising at least three separate fusion proteins of which at least two are different, each fusion protein comprising a leucine zipper domain of the sequence LEALKEK (SEQ ID NO: 1) or LKALEKE (SEQ ID NO: 4) and an alpha or beta IL-2 receptor subunit ectodomain, the leucine zipper domains of said at least three separate fusion proteins non-covalently binding to one another, and said receptor subunit ectodomains forming a high affinity binding complex for the ligand for a native IL-2 receptor.

2. The hetero-oligomeric high affinity binding complex of claim 1, said complex is purified.

3. The purified hetero-oligomeric high affinity binding complex of claim 2 further comprising a pharmaceutically acceptable excipient.

4. A high affinity IL-2 heterotrimeric binding complex comprising three fusion proteins, namely a first fusion protein, a second fusion protein and a third fusion protein, said first and second fusion proteins each comprising an alpha IL-2 receptor subunit ectodomain and a leucine zipper domain consisting of a seven heptad repeat of an amino acid of a sequence LEALKEK (SEQ ID NO: 1), said third fusion protein comprising a beta IL-2 receptor subunit ectodomain and a leucine zipper domain consisting of a seven heptad repeat of an amino acid of the sequence LKALEKE (SEQ ID NO: 4), the leucine zipper domains of each of said first, second and third fusion proteins non-covalently binding to one another, whereby the ectodomains of each are positioned so as to form in combination a high affinity IL-2 binding complex.

5. The hetero-oligomeric high affinity binding complex of claim 4 said complex is purified.

6. The purified hetero-oligomeric high affinity binding complex of claim 5 further comprising a pharmaceutically acceptable excipient.

7. A synthetic leucine zipper polypeptide comprising a heptad repeat amino acid sequence consisting of SEQ ID NO: 1 or SEQ ID NO: 4 covalently attached to an ectodomain of an alpha or beta IL-2 receptor subunit.

8. A polynucleotide comprising a nucleotide sequence encoding said polypeptide of claim 7.

9. The polynucleotide of claim 8 further comprising appropriate promoter and control sequences to enable the expression of said polynucleotide.

10. A polynucleotide comprising a nucleotide sequence encoding a fusion protein, said fusion protein comprising an alpha or beta IL-2 receptor subunit ectodomain of said high affinity IL-2 binding complex a fused protein, wherein the fused protein comprises the leucine zipper domain that comprises one or more repeats of an amino acid of the sequence LEALKEK (SEQ ID NO: 1 or LKALEKE (SEQ ID NO: 4).

11. The polynucleotide in accordance with claim 10 being a DNA molecule.

* * * * *